(12) United States Patent
Madhavamenon et al.

(10) Patent No.: US 10,624,942 B2
(45) Date of Patent: *Apr. 21, 2020

(54) COMPOSITION FOR AMELIORATION OF PERI- AND POST-MENOPAUSAL SYMPTOMS AND A PROCESS FOR PRODUCING THE SAME

(71) Applicant: AKAY FLAVOURS & AROMATICS PVT. LTD., Kerala (IN)

(72) Inventors: Krishnakumar Illathu Madhavamenon, Kerala (IN); Balu Paulose Maliakel, Kerala (IN); Shamshad Begum Saddapalli, Karnataka (IN); Jayalakshmi Hosakere Krishnamurthy, Karnataka (IN); Geetha Kalaiah, Karnataka (IN); Vasundhara Mariappa, Karnataka (IN); Suresha Sanaba Venkataiah, Karnataka (IN)

(73) Assignee: AKAY FLAVORS & AROMATICS PVT, LTD., Kerala (IN)

( * ) Notice: Subject to any disclaimer, the term of this patent is extended or adjusted under 35 U.S.C. 154(b) by 91 days.

This patent is subject to a terminal disclaimer.

(21) Appl. No.: 15/830,011

(22) Filed: Dec. 4, 2017

(65) Prior Publication Data

US 2018/0092956 A1 Apr. 5, 2018

Related U.S. Application Data

(63) Continuation of application No. 14/856,584, filed on Sep. 17, 2015, now Pat. No. 9,855,308.

(30) Foreign Application Priority Data

Sep. 19, 2014 (IN) .......................... 4573/CHE/2014

(51) Int. Cl.

| | | |
|---|---|---|
| *A61K 36/48* | (2006.01) |
| *A61K 31/355* | (2006.01) |
| *A61K 9/16* | (2006.01) |
| *A61K 9/00* | (2006.01) |
| *A61K 31/198* | (2006.01) |
| *A23L 33/00* | (2016.01) |
| *A23L 33/11* | (2016.01) |
| *A23L 33/15* | (2016.01) |
| *A23L 33/16* | (2016.01) |
| *A61K 31/4406* | (2006.01) |
| *A61K 31/58* | (2006.01) |
| *A61K 31/7042* | (2006.01) |
| *A61K 33/06* | (2006.01) |
| *A61K 31/194* | (2006.01) |
| *A61K 31/455* | (2006.01) |
| *A61K 31/7048* | (2006.01) |
| *A61K 31/736* | (2006.01) |
| *A61K 38/00* | (2006.01) |

(52) U.S. Cl.

CPC .............. *A61K 36/48* (2013.01); *A23L 33/11* (2016.08); *A23L 33/15* (2016.08); *A23L 33/16* (2016.08); *A23L 33/40* (2016.08); *A61K 9/0053* (2013.01); *A61K 9/16* (2013.01); *A61K 31/194* (2013.01); *A61K 31/198* (2013.01); *A61K 31/355* (2013.01); *A61K 31/4406* (2013.01); *A61K 31/455* (2013.01); *A61K 31/58* (2013.01); *A61K 31/7042* (2013.01); *A61K 31/7048* (2013.01); *A61K 31/736* (2013.01); *A61K 33/06* (2013.01); *A61K 38/00* (2013.01); *A23V 2002/00* (2013.01); *A61K 38/00* (2013.01); *A61K 2236/15* (2013.01); *A61K 2236/33* (2013.01); *A61K 2236/333* (2013.01); *A61K 2236/37* (2013.01); *A61K 2236/39* (2013.01); *A61K 2236/51* (2013.01)

(58) Field of Classification Search

None
See application file for complete search history.

(56) References Cited

U.S. PATENT DOCUMENTS

| | | |
|---|---|---|
| 5,707,630 A | 1/1998 | Morrow |
| 6,248,307 B1 | 6/2001 | Borneman et al. |
| 8,217,165 B2 | 7/2012 | Goel |
| 9,855,308 B2 * | 1/2018 | Madhavamenon .... A61K 36/48 |
| 2008/0199517 A1 | 8/2008 | Sunil et al. |
| 2010/0004070 A1 | 1/2010 | Bulpett et al. |

FOREIGN PATENT DOCUMENTS

| | | |
|---|---|---|
| KR | 101348471 B1 | 2/2014 |

OTHER PUBLICATIONS

Gerd Assmann, Jilko Schriewer, Gerd Schmitz and Edgar-Otto Hagele, "Qualification of High Density Lipoprotein Cholesterol by Precipitation With Phosphotungstic Acid/ MgCl2" Clin. Chem. 29/12, 2026-2030 (1983).

David M. DeLong; Elizabeth R. DeLong; Peter D. Wood; Kenneth Lippel; Basicl M. Rifkind, "aComparison of Methods for the Estimation of Plasma Low- and Very Low-Density Lipoprotein Cholesterol" Clinical Investigation, the Lipid Research Clinics Prevalence Study. JAMA, Nov. 7, 1986 vol. 258 No. 17. Downloaded from: http://jama.jamanetwork.com/ by a New York University User on Jun. 4, 2015.

Derrick B. Jelliffe, "The Assessment of the Nutritional Status of the Community" Work Health Organization Monograph Series No. 53. 1966. Printed in Switzerland.

(Continued)

*Primary Examiner* — Susan Hoffman

(74) *Attorney, Agent, or Firm* — Mark M. Friedman

(57) ABSTRACT

The present invention provides a nutraceutical composition, a process for the preparation of the nutraceutical composition useful for amelioration of pen- and post-menopausal symptoms in women. The nutraceutical composition is stable, directly compressible, water soluble, free flowing form having particle size not more than 2.0 μm comprising extract of *Trigonella foenum-graecum*, at least one bioavailable form of magnesium and vitamin E. The present invention also provides a method of treating ameliorating, treating and/or preventing pen- and post-menopausal discomforts in a subject suffering from pen- or post-menopausal symptoms comprising administering to the subject a therapeutically effective amount of the nutraceutical composition.

10 Claims, 6 Drawing Sheets

(56) References Cited

OTHER PUBLICATIONS

Jennifer S. Lee, Bruce Ettinger, Frank Z. Stanczyk, Eric Vittinghoff, Vladimir Hanes, Jane A. Cauley, Walt Chandler, Jim Settlage, Mary S. Beattie, Elizabeth Folkerd, Mitch Dowsett, Deborah Grady, Steven R. Cummings: "Comparison of Methods to Measure Low Serum Estradiol Levels in Postmenopausal Women", The Journal of Clinical Endocinology & Metabolism , Oct. 2006, 91(10):3791-3797. Copyright(c) 2006 by The Endocrine Society DOI:10.1210/jc.2005-2378.

William E. Neeley, "Simple Automated Determination of Serum or Plasma Glucose by a Hexokinase/Glucose-6-Phosphate Dehydrogenase Method", Institute of Pathology, Case Western Reserve University School of Medicine, Cleavland Ohio. Accepted Mar. 20, 1972. Clinical Chemistry vol. 18, No. 6, 1972.

Nanette Santoro, C. Neill Epperson, Sarah B. Mathews. "Meanopausal Symptoms and Their Management". Endocrinol Metab Clin N Am 44 (2015) 497-515. 2015 Elsevier Inc. endo.theclinics.com.

J. Stern, W.H.P. Lewis, "The Colorimetric Estimation of Calcium in Serum With o-Cresolphthalein Compexone" Clinica Chimica Acta, vol. 2 (1957).

John E. Ware, Jr. and Cathey Donald Sherbourne. "The MOS 36-Item, Short-Form Health Survey (SF-36): I. Conceptual Framework and Item Selection". Medical Care vol. 30, No. 6. Jun. 1992, pp. 473-483. Published by: Lippincott Williams & Wilkins. http://www.jstor.org/stable/3765916.

Rolf Deeg, Joachim Ziegenborn. "Kinetic Enzymic Method for Automated Determination of Total Cholesterol in Serum" Clin. Chem. 29/10, 1798-1802 (1983).

\* cited by examiner

COMPOSITION FOR AMELIORATION OF PERI- AND POST-MENOPAUSAL SYMPTOMS AND A PROCESS FOR PRODUCING THE SAME

TECHNICAL FIELD

The present invention relates to a plant-based nutraceutical composition and a process for the preparation of the nutraceutical composition useful for amelioration of peri- and post-menopausal symptoms in women.

BACKGROUND

Menopause is the transition from the reproductive stage to the non-reproductive stage of a woman's life and is characterized primarily by the cessation of menstruation. At this stage, the ovaries have stopped releasing eggs and production of most of their estrogen. Peri-menopause or "menopause transition" can begin 8 to 10 years before menopause, when the ovaries gradually produce less estrogen. It usually starts in a woman's 40s, but can start in the 30s as well. Perimenopause lasts up until menopause, the point when the ovaries stop releasing eggs. In the last 1 to 2 years of peri-menopause, the drop in estrogen accelerates. At this stage, many women can experience menopause symptoms. Post-menopause is the years after menopause. During this stage, menopausal symptoms, such as hot flashes, can ease for most women but still occur.

The discomforts due to the hormonal variations experienced during menstruation, stage of approaching menopause or during menopause, are often referred to as postmenopausal syndrome or PMS. Menopausal symptoms and problems due to hormonal imbalance and nutritional deficiency arise and are associated with a variety of symptoms. It is not a disease, but a stage of life which necessitates proper attention and nutrition. The intensity of the symptoms vary amongst individuals and generally include aches, hot flashes, rapid heartbeats, irritability, fatigue, insomnia, nervousness, high levels of stress, extreme sweating, headaches, frequent urination, early wakening, vaginal dryness, mood swings, depression, dizziness, cardiac symptoms and various physiological changes leading to poor quality of life (Santoro et al., 2015).

Low estradiol levels, anemia and rise in cholesterol and triglyceride levels are also associated with PMS conditions. Menopause is also characterized by osteoporosis or loss of bone density, resulting in increased bone fractures and vertebral column collapse due to low serum calcium levels. In the long run, women become susceptible to cardiovascular diseases, osteoporosis and cancer due to falling levels of estrogen and progesterone hormones.

Since menopause is associated with a state of hypoestrogenism, conventional treatments for treating menopausal symptoms include pharmaceutical drugs and hormone replacement therapy (HRT). Pharmaceutical drugs alleviate discomfort caused by menopausal symptoms but these are known to cause mild or severe side-effects. The drugs also provide short-term relief without any benefits lasting for long time. HRT consists of administering either estrogen hormone, or estrogen hormone in combination with progesterone hormone to artificially boost hormone levels. However, HRT may have undesirable side effects, such as headache, diarrhea, nervousness, and is associated with risks of developing cancers (breast and uterine) and cardiovascular disease. HRT provides only a short-term relief and is expensive.

Complementary and alternative therapies and nutraceutical supplementation with safe natural agents, especially from herbs, is a widely accepted practice all over the world. Their use as natural hormonal agents is preferred as they are considered safe and harmonious with the values, beliefs and life styles of people. These agents also effectively try to bridge the gap in heightened nutritional and hormonal requirements of a woman during this phase and help in the metabolism and absorption of the essential nutrients into the body. Such agents, generally referred to as plant phytoestrogens appear to have both estrogenic and anti-estrogenic effects and are suitable candidates for selective estrogen receptor modulators (SERMs) instead of hormone replacement therapy. Presently, various botanicals are utilized for treating menopausal symptoms in women.

U.S. Pat. No. 5,707,630 describes a herbal compound for relief of PMS through menopausal symptoms comprising red raspberry, black cohosh, capsicum, cascara sagrada, damiana, ginger, valerian and a binding agent.

U.S. Pat. No. 6,248,307 describes a composition having at least one herbal compound and at least one homeopathic drug that is useful for treating symptoms associated with menopause. The homeopathic drug is selected from the group consisting of *Amyl nitrosum, Lachesis muta* and *Sanguinaria canadensis* and the herbal component comprises *Cimicifuga racemosa*.

KR101348471 (B1) describes a composition containing a *Larrea cuneifolia* Cay. extract to obtain phytoestrogen compounds, which effectively prevents, treats, and relieves menopausal symptom including hot flashes, osteoporosis, thrombosis, and atrophic vaginitis.

US20100040708 describes a herbal composition for treating menopausal symptoms in a woman comprising yarrow, damiana, skullcap, chaste tree berry, wild yam, corn silk, cramp bark, bloodroot, fenugreek, feverfew, cardamom and *Panax ginseng*.

Most herbal compositions and compositions of traditional medicine systems usually treat only a few of the menopausal symptoms, and are incapable of providing relief from most or all of the menopausal symptoms. Further, as the conventional herbal compositions include many wild collected herbs in powder form which usually have different levels of bioactive compounds and contaminants like heavy metals like lead, arsenic, mercury, etc., they are difficult to standardize. Post harvesting operations such as drying of these herbals usually does not have any uniform procedures, which affect the phytochemical composition and microbial load with unhealthy effects. The conventional compositions also suffer from the problem of requirement of huge volumes of the raw materials to achieve the desired therapeutic effective amount and lack in ease of storage and handling. Sometimes the problem of identifying and/or accessing the exotic, unfamiliar or unconventional raw ingredients, plants/herbs, becomes a tedious and cumbersome procedure. The problems often culminate towards less patient compliance and often deter the patient from pursuing effective and safe alternative therapies.

Accordingly, there exists an urgent need for a composition that is primarily of edible plant origin preferably from a well-known food component having the history of and safe consumption for centuries. Possibility of organic cultivation and known post-harvest operations such raw materials will add the value of the composition since it can be produced with full traceability in organic quality. Such composition from food components that provide effective management of menopausal symptoms while obviating the drawbacks of conventional therapies of HRT and pharmaceutical drugs is of great significance.

SUMMARY

In a first aspect, there is provided a nutraceutical composition comprising extract of *Trigonella foenum-graecum*; at least one bioavailable form of magnesium and vitamin E characterized in that the composition is stable, directly compressible, water soluble, free flowing form having particle size not more than 2.0 μm. The extract of *Trigonella foenum-graecum* comprises phytoestrogens comprising at least one of a steroidal saponin selected from the group comprising protodioscin, diosgenin and yamogenin; an alkaloid, trigonellin; and, a natural amino acid, 4-hydroxyisoleucine.

Advantageously, the nutraceutical composition comprises enriched bioactive fractions of fenugreek in a stable form to help alleviate peri- and post-menopausal symptoms, control hormonal imbalance, elevate estrogen levels, provide cardiac health protective effects and improve the quality of life without affecting dietary intake, body weight or other anthropometric measurements in women suffering from peri- and post-menopausal symptoms.

In an aspect, the nutraceutical composition comprises protodioscin in the range of about 5 to 20 g, trigonellin in the range of about 1 to 8 g, 4-hydroxyisoleucine in the range of about 1 to 10 g, proteins in the range of about 1 to 15 g, carbohydrates in the range of about 5 to 25 g, dietary fibers in the range of about 2 to 15 g, fat in the range of about 2-10 g, vitamin E in the range of about 5 to 20 g and magnesium citrate in the range of about 10 to 25 g in 100 g dry powder of the composition.

Advantageously, the nutraceutical composition provides a synergistic effect on efficacy in PMS suffering individuals as a reduced dose of magnesium salt and vitamin E in combination with the phytoestrogen and phytonutrient rich fraction of fenugreek results in therapeutically effective management of the menopausal symptoms. The intake levels of magnesium salt and vitamin E is reduced compared to the recommended levels in pharmacological therapies.

In another aspect, the present disclosure is economically advantageous as it employs indigenous sourced relatively inexpensive kitchen spice as starting materials which distinctly reduce the costs while providing organic quality traceability.

Another aspect of the present disclosure provides a process of preparing a nutraceutical composition comprising fractionating the fenugreek seeds for targeted extraction and enrichment of desired phytonutrients for delivering beneficial effect on postmenopausal women and women approaching menopause such that 1 gram of the nutraceutical composition provides an bioactive extract equivalent dose of 15 to 30 g of fenugreek seeds.

Advantageously, the process provides a nutraceutical composition for easy in-vivo absorption. The soluble fiber fraction helps to make the composition form into a stable encapsulated powder with direct compressibility and the natural matrix comprising proteins, carbohydrates, fats and dietary fiber provides the existence of the phytonutrients in stable water soluble, powder form suitable for solid oral dosage formulations.

One more aspect of the present disclosure provides a method of ameliorating, treating and/or preventing peri- and post-menopausal discomforts in a subject suffering from peri- or post-menopausal symptoms comprising administering to the subject a therapeutically effective amount of the nutraceutical composition comprising extract of *Trigonella foenum-graecum*; at least one bioavailable form of magnesium and vitamin E.

In another aspect, the nutraceutical composition provides effective management of PMS comprising administering to a subject a daily dose from about 0.25 to about 2.0 g of the composition for a period of time from 10 to 100 days to reduce the severity, frequency or both of a menopausal symptom.

In yet another aspect, the nutraceutical composition is administered as a hormone replacement therapy, a dietary and/or a nutrient supplement.

The foregoing has outlined some of the most pertinent objects of the invention. These objects should be construed to be merely illustrative of some of the more prominent features and applications of the intended invention. The invention includes other features and advantages which will be described or will become apparent from the following more detailed description of the embodiment.

BRIEF DESCRIPTION OF THE DRAWINGS

The foregoing summary, as well as the following detailed description of the invention will be better understood when read in conjunction with the appended drawings. For the purpose of assisting in the explanation of the invention, there are shown in the drawings embodiments which are presently preferred and considered illustrative. It should be understood, however, that the invention is not limited to the images shown therein. In the drawings.

DETAILED DESCRIPTION

Figure 1:
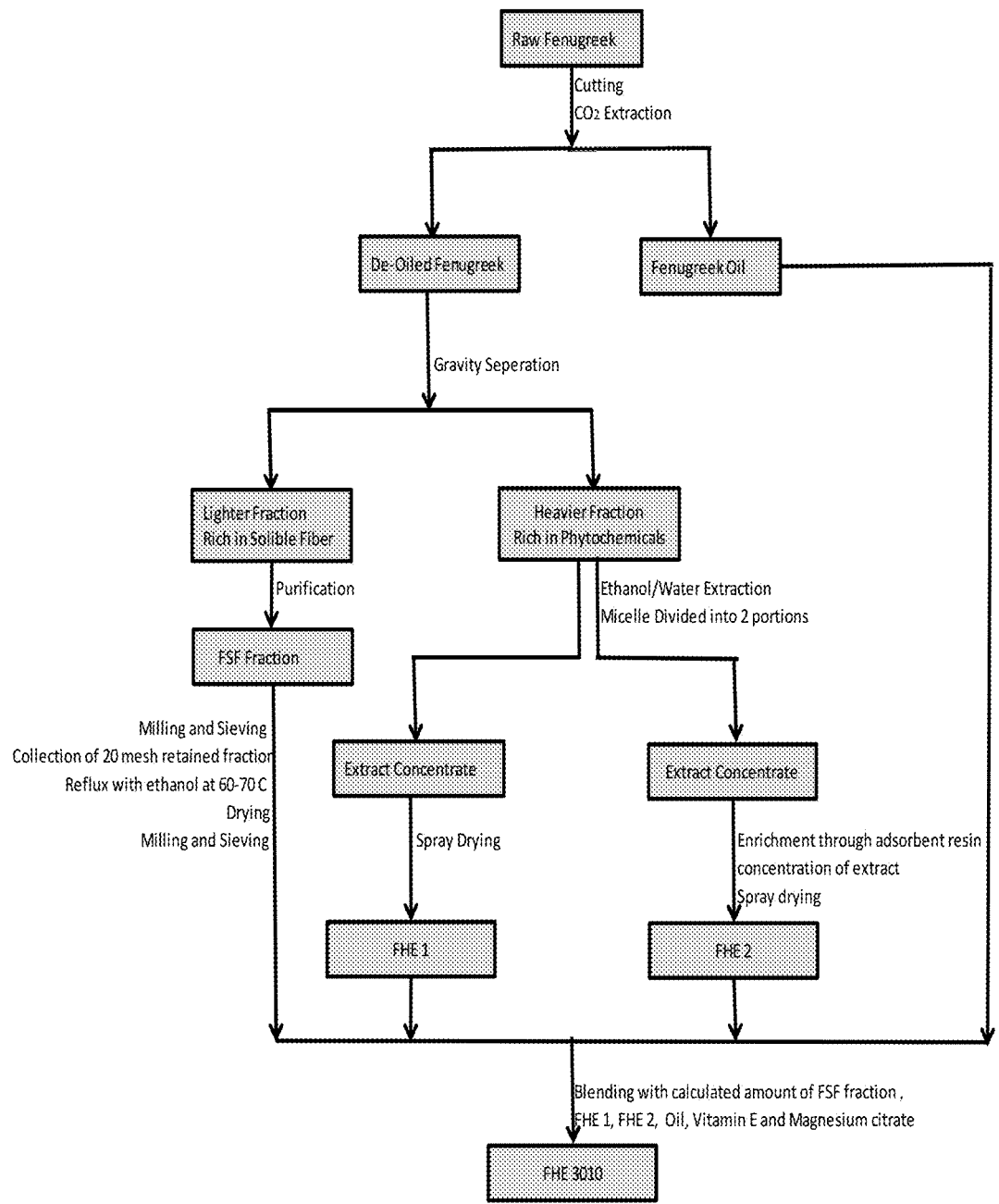
FIG. 1 is a flow chart depicting the process for producing a nutraceutical composition (FHE-3010).

The present invention will now be described more fully herein after. For the purposes of the following detailed description, it is to be understood that the invention may assume various alternative variations and step sequences, except where expressly specified to the contrary. Thus, before describing the present invention in detail, it is to be understood that this invention is not limited to particularly exemplified systems or embodiments that may of course, vary.

Unless otherwise defined, all terms technical and scientific used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention.

As used herein, the singular forms "a," "an," and "the" include plural reference unless the context clearly dictates otherwise. The term "and/or" means one or all of the listed elements or a combination of any two or more of the listed elements.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "around", "about" or "approximately" shall generally mean within 20 percent, preferably within 10 percent, and more preferably within 5 percent of a given value or range. Numerical quantities given herein are approximate; meaning that the term "around", "about" or "approximately" can be inferred if not expressly stated. When the term "about" is used in describing a value or an endpoint of a range, the disclosure should be understood to include both the specific value and end-point referred to.

As used herein, the terms "comprising" "including," "having," "containing," "involving," and the like are to be understood to be open-ended, i.e., to mean including but not limited to.

As used herein, the term "pharmaceutically or therapeutically effective amount" refers to the amount of the active ingredient, the extract, to be administered orally to the subject to trigger the desired effect without or causing minimal toxic adverse effect against the subject. One skilled in the art should know that the effective amount can vary from one individual to another due to the external factors such as age, sex, diseased state, races, body weight, formulation of the extract, availability of other active ingredients in the formulation and so on.

As used herein, the terms 'fenugreek' and '*Trigonella foenum-graecum L.*' are used interchangeably.

As used herein, the term "peri-menopause" is associated with menopausal transition. The term means 'around menopause' and refers to the time period during which a woman's body makes its natural transition toward permanent infertility.

As used herein, the term "menopause" is the point when a woman no longer has menstrual periods. At this stage, the ovaries have stopped releasing eggs and producing most of their estrogen.

As used herein, the term "post-menopausal" denotes the years of peri and after menopause, when a women starts experiencing the discomforts and menstrual irregularity or permanent stop of menses owing to the hormonal imbalance The present invention provides a nutraceutical composition comprising enriched phytonutrients of fenugreek, *Trigonella foenum-graecum L.*, exhibiting beneficial physiological and pharmacological effects on women who are experiencing the discomforts of peri-menopausal, menopausal and post-menopausal symptoms encountered due to hormonal variations. The present invention solves the problems associated with currently used compositions and various traditional systems for treatment of the menopausal symptoms associated with various stages in a woman's life.

The present inventors have surprisingly and unexpectedly found that the nutraceutical composition exhibits beneficial synergistic effect on the amelioration of menopausal symptoms and in relieving the issues and discomforts related to hormonal imbalance and PMS in the target group of peri- and post-menopausal women without significant anthropometric changes or body weight gain or any adverse effects. The concentrated content of fenugreek phytonutrients effectively helps in reducing the intake of the magnesium citrate content and vitamin E which is normally prescribed to PMS suffering individuals at relatively high levels of 1 to 1.5 g/day of vitamin E and 250 to 350 mg of magnesium/day.

The present invention is economically advantageous as it employs indigenous sourced relatively inexpensive kitchen spice as starting materials which distinctly reduce the costs. The present invention also facilitates an effective and focused management of the discomforts associated with peri- and post-menopausal stages.

Disclosed herein is a nutraceutical composition enriched with the phytonutrients of fenugreek seeds such that the nutraceutical composition provides phytoestrogenic compounds and other bioactive phytochemicals in a significantly higher amount over that usually found in naturally occurring conditions. One gram of the nutraceutical composition provides an extract equivalent dose of 15 to 30 g of fenugreek seeds, which is a normal consumption level of fenugreek in traditional systems. The composition is particularly advantageous as the solid oral composition is prepared using minimal additives and excipients and achieves the desired solid formulation using specific combinations of the extract components to achieve a nutraceutical composition rich in phytoestrogenic components. Despite the tremendous advancements in drug delivery, the oral route remains as the perfect route for the administration of therapeutic agents because of the low cost of therapy, ease of administration, patient convenience and compliance. This is also the most preferred route for food supplements and nutraceuticals comprising phytonutrients, minerals and vitamins.

In an embodiment, a nutraceutical composition comprising extract of *Trigonella foenum-graecum*; at least one bioavailable form of magnesium and vitamin E is provided such that the composition is stable, directly compressible, water soluble, free flowing form having particle size not more than 2.0 μm. The extract of *Trigonella foenum-graecum* comprises phytoestrogens comprising at least one of a steroidal saponin selected from the group comprising protodioscin, diosgenin and yamogenin; an alkaloid, trigonellin; and, a non-proteinogenic amino acid, 4-hydroxyisoleucine.

In another embodiment, the composition comprises a therapeutically effective amount of the extract of *Trigonella foenum-graecum*, a therapeutically effective amount of at least one bioavailable form of magnesium and a therapeutically effective amount of vitamin E. The therapeutically effective amount of the extract of *Trigonella foenum-graecum* comprises a therapeutically effective amount of at least one of a phytoestrogen, a steroidal saponin, an alkaloid and a non-proteinogenic amino acid.

In yet another embodiment, the phytoestrogens present in 1 g of the composition is at an equivalent dose of 15 to 30 g of *Trigonella foenum-graecum* seeds in natural state.

Appropriate saponins include without limitation, protodioscin, diosgenin, and yamogenin. Appropriate alkaloids include without limitations trigonellin. Appropriate non-proteinogenic amino acid include without limitations 4-hydroxyisoleucine. Appropriate natural fat include without limitations oil.

Appropriate vitamin E components include tocopherols and tocotrienols. Appropriate tocopherols include without limitations alpha-, beta-, gamma-, or delta-tocopherol alone or a mixture thereof in free form or its salt form such as acetate.

Appropriate bioavailable forms of magnesium include without limitations magnesium oxide, magnesium citrate, magnesium hydroxide, and magnesium stearate or any other form suitable for supplementation.

In another embodiment, the composition comprises extract of *Trigonella foenum-graecum*; at least one bioavailable form of magnesium and vitamin E and at least one of a protein fraction, a carbohydrate fraction, a fat fraction, a fiber fraction, or a combination thereof, wherein the fractions are derived from fenugreek seeds.

In yet another embodiment, the composition comprises a therapeutically effective amount of the extract of *Trigonella foenum-graecum*, a therapeutically effective amount of at least one bioavailable form of magnesium, a therapeutically effective amount of vitamin E and at least one of a protein fraction, a carbohydrate fraction, a fat fraction, a fiber fraction, or a combination thereof Appropriate proteins include without limitations those derived from fenugreek seeds, food-grade proteins and peptides.

Appropriate carbohydrates include without limitations those derived from fenugreek seeds and food-grade carbohydrates.

Appropriate micronutrients include without limitations Vitamin E, Vitamin C, Vitamin B, and minerals like magnesium, iron, and calcium.

Appropriate fibers include without limitations those derived from fenugreek seeds or plants like guar gum, psyllium seeds, tamarind seeds and gum ghatti having a gum like character and encapsulating property.

The fraction of fat, fiber, protein and carbohydrates works as a matrix for the encapsulation of phytoestrogenic saponins, alkaloids and amino acid to form stable powders. Additionally, the high requirement for any external additives as excipients is negated for rendering the composition suitable for preparation of solid oral dosage forms.

In another embodiment, the addition of external additives as excipients to render the composition into suitable formulations is provided.

In a further embodiment, the composition comprises a therapeutically effective amount of extract of *Trigonella foenum-graecum*; a therapeutically effective amount of vitamin E, a therapeutically effective amount of magnesium citrate, wherein the extract of *Trigonella foenum-graecum* comprises a therapeutically effective amount of protodioscin, trigonellin, 4-hydroxyisoleucine, proteins, carbohydrates, fats and dietary fiber.

In yet another embodiment, the nutraceutical composition comprises protodioscin in the range of about 5 to 20 g, trigonellin in the range of about 1 to 8 g, 4-hydroxyisoleucine in the range of about 1 to 10 g, proteins in the range of about 1 to 15 g, carbohydrates in the range of about 5 to 25 g, dietary fibers in the range of about 2 to 15 g, fat in the range of about 2 to 10 g, vitamin E in the range of about 5 to 20 g and magnesium citrate in the range of about 10 to 25 g in 100 g dry powder of the composition.

Another embodiment of the present invention provides suitable forms of the nutraceutical composition suitable for administration in the oral, parenteral, rectal or transdermal mode.

Appropriate forms include without limitations a solid, semi-solid and liquid form. Useful solid form preparations include powders, pills, tablets, dispersible granules, capsules, cachets and suppositories. Useful liquid form preparations include solutions, suspensions, syrup, vials, drops and emulsions. Also useful are solid form preparations which are intended to be converted, shortly before use, to liquid form preparations for either oral or parenteral administration. Such liquid forms include solutions, suspensions and emulsions. Also useful are solid forms that are enteric-coated for sustained release of the composition.

In another embodiment, the nutraceutical composition forms are suitable for administration in the oral, parenteral, rectal or transdermal mode. Water or water-propylene glycol solutions for parenteral injection or addition of sweeteners and opacifiers for oral solutions, suspensions and emulsions may be intended.

In yet another embodiment, the nutraceutical composition is in the form of an orally administrable dietary supplement or a nutrient supplement.

In a further embodiment, the nutraceutical composition may comprise additional components like excipients, additives, binders, thickening agents useful for the preparation of desired formulations. Non-limiting examples include non-toxic compatible fillers, binders such as starch, polyvinyl pyrrolidone or cellulose ethers, disintegrants such as sodium starch glycolate, crosslinked polyvinyl pyrrolidone or croscarmellose sodium, buffers, preservatives, anti-oxidants, lubricants, flavorings, thickeners, coloring agents, wetting agents such as sodium lauryl sulfate, emulsifiers and the like. The amount of excipient or additive can range from about 0.1 to about 95 weight percent of the total weight of the treatment composition or therapeutic combination. One skilled in the art would understand that the amount of carrier(s), excipients and additives (if present) can vary.

Disclosed herein is a process for producing a composition enriched with bioactive components of interest from fenugreek for the amelioration of peri- and post-menopausal symptoms in women who are experiencing the discomforts of pen-menopausal, menopausal and post-menopausal symptoms. Advantageously, the process disclosed herein provides a selective enrichment of the bioactive fractions of the fenugreek seeds so as to produce a nutraceutical composition comprising phytoestrogens in 1 g of the composition equivalent to a dose of 15 to 30 g of *Trigonella foenum-graecum* seeds in natural state.

Often plant extracts are prepared using water, alcohol, water-alcohol mixture and other organic solvents; however, for compaction into solid dose formulations, these extractions often necessitate the addition of synthetic excipients or additives to change into stable free flowing powders. Therefore, preparing a formulation which is high in phytonutrients without any loss in the concentration by the addition of excipients or additives is a challenging task, which is addressed in this invention by employing the soluble dietary fiber, galactomannan, isolated and purified from the fenugreek seeds itself Owing to the gum-like character and encapsulating property, fenugreek soluble fiber produced in this invention is employed as a natural excipient for producing stable and encapsulated fenugreek phytonutrients suitable for the nutraceutical composition into an oral formulation. A 3 to 5% of the soluble fiber component results in a composition that is a directly compressible granular powder.

Accordingly, the present invention provides a process for preparing the composition enriched with fenugreek phytonutrients in a stable encapsulated free flowing granular and directly compressible powder form. The process disclosed herein is safe and non-toxic as only water and ethanol is employed for the isolation of phytochemicals from fenugreek husks. Diagrammatic representation of the preparation was mentioned in FIG. 1. The process consists of extraction of phytochemicals from the fenugreek seeds by separating the seeds into three major components for preparing the fenugreek oil, fenugreek soluble fiber fraction, fenugreek husk extract.

Advantageously, disclosed herein is a process for physical separation of bioactive components of fenugreek seeds into phytoestrogen and other phytochemicals rich water insoluble fraction and soluble dietary fiber rich water soluble fraction suitable for the easy extraction of phytochemicals in water soluble form. The present invention provides a process of aqueous or hydro-alcoholic extraction by which saponins are quantitatively extracted from fenugreek husk obtained by separating the soluble dietary fiber rich endosperm of fenugreek seeds. The composition is rich in all the essential phytonutrients and phytoestrogens in a water soluble form by extraction and subsequent purification with only water and ethyl alcohol in organic quality.

The selectively separated fractions of the seed parts are extracted, concentrated, purified and blended into a compact blend rich in phytoestrogen and phytochemical components of the fenugreek seeds using a hydro-ethanolic process without using any other organic solvents. The composition of the fenugreek extract is a rich source of dietary fiber including galactomannan soluble fiber and insoluble fiber, phytochemicals, alkaloids, flavanoids, amino acids, protein and carbohydrates. The extract prepared from the saponin rich fenugreek husk shows excellent phytoestrogenic properties as seen from the rise in blood estradiol levels in women having PMS. The phytoestrogens are effective in managing the imbalance during post-menopause.

Advantageously, the nutraceutical composition rich in phytonutrients produced by this process is stable, water soluble, free flowing, directly-compressible solid form having a particle size not more than 2.0 µm. The sub-micronised particles of the composition are very effective in high levels and ease of in-vivo absorption of the bio-actives and phytonutrients.

The composition produced by the process has the bioactive molecules in their natural matrices containing proteins, carbohydrates and dietary fibre in a water soluble form, all components preferably obtained from the different fractions of the seeds of fenugreek. The desired compounds to be extracted from the alcohol/aqueous extracts of are mainly constituted of, but not limited to, phytoestrogens, alkaloids, amino acids, proteins, lipids, saccharides, and small peptides. Due to polarity of these compounds, the polar solvent such as water, alcohol or acetone is found to be effective in extracting these desired compounds from the plant matrix.

One embodiment provides a process for preparing a nutraceutical composition rich in phytonutrients, preferably phytoestrogens from the mature and dried fenugreek seed husks for ameliorating, treating and/or preventing peri- and post-menopausal discomforts in a subject suffering from peri- or post-menopausal symptoms.

Another embodiment provides a process for producing a nutraceutical composition is provided comprising:

(a) mechanically reducing the seeds of *Trigonella foenum-graecum* to obtain size-reduced particles,
(b) subjecting the particles of step (a) to solvent extraction to obtain an Extract A,
(c) separating the particles of step (a) or the extracted particles of step (b) into lighter and heavier fractions based on their density using a gravity separator,
(d) subjecting the lighter fraction obtained from step (c) to solvent extraction and subsequent drying to obtain an Extract B,
(e) subjecting the heavier fraction obtained from step (c) to solvent extraction to obtain a micelle,
(f) separation of the micelle of step (e) into two portions whereby
   (i) the first portion is concentrated under reduced pressure to obtain a liquid phytonutrient rich Extract C having phytoestrogen content in the range of 3 to 8% protodioscin,
   (ii) the second portion is concentrated and purified to obtain a phytonutrient rich liquid Extract D having phytoestrogen content in the range of 10 to 40% protodioscin,
(g) evaporation of the liquid extracts of step (f) such that the water content is 70 to 90% and ethanol content less than 0.5%,
(h) blending vitamin E with the Extract A obtained from step (b) and further mixing into a 1 to 3% water solution of Extract B obtained from step (d) followed by addition of the Extract C and Extract D of step (g) with at least one bioavailable form of magnesium to form a nutraceutical composition,
wherein the ratio of Extract C to Extract D is in the range of about 4:1 to about 1:4, and the resulting blend is stable, and water soluble having particle size preferably less than 2 µm, suitable for the conversion into free flowing powder or granular form.

Appropriate blends of fractions of Extract C to Extract D is at 4:1 to 1:4 ratio, preferably at 3:1 to 1:3 ratio and more preferably at 1:1 ratio.

Appropriate mechanical reduction of the fenugreek seeds is achieved by but not limited to any of the methods of cutting, flaking and powdering to a particle size of less than 5 mm, preferably to a particle size of 0.5 mm to about 1.5 mm.

Appropriate extraction of the reduced or powdered seed particles is carried out by steam distillation, solvent extraction with aliphatic alkanes or supercritical fluid extraction such that the oil fraction is extracted without extraction of the phytochemicals. The phytochemicals are therefore left intact in the residual powdered component for further processing.

In an embodiment, solvent extraction is carried out by organic solvents alone or in combination with water. Appropriate solvents include without limitations, lower aliphatic alcohols, lower aliphatic ketones, aliphatic alkanes and mixtures thereof.

Appropriate methods of concentration include without limitations, evaporation under reduced pressure using any suitable technology prevalent such as thin film evaporations or the like. Preferably, the evaporation is carried out at reduced pressure at about 600 to 700 atmosphere and at a temperature below 50° C.

Appropriate methods of purification include without limitations chromatography, precipitation and liquid-liquid extraction, preferably adsorption and ion-exchange chromatography.

Appropriate methods of drying include without limitations, spray-drying, freeze frying, evaporation, and drying under reduced pressure.

The soluble fiber fraction, Extract B, helps to make the composition a stable encapsulated powder with direct compressibility due to the gum like character, film-forming capacity and high viscosity of the soluble fiber.

In another embodiment, the process provides a blend comprises Extract A and Extract B with vitamin E and at least one bioavailable form of magnesium to form a nutraceutical composition having stable, readily compressible, water soluble, free flowing form.

The present inventors have surprisingly found that the oil fraction of the fenugreek seeds extracted as Extract A is a phytoestrogenic bioactive emulsifying agent which along with the soluble fiber Extract B acting as a binding agent lends to form a stable matrix for the composition rich in phytoestrogens and phytonutrients of fenugreek in a stable, water soluble, compressible form. Such stable, water soluble, compressible form of phytonutrient rich compositions can be easily formulated into solid, oral dosage forms without requiring external additives or excipients thereby, not diluting the biologically active phytonutrient content in the formulation.

In an embodiment, a nutraceutical composition is prepared using the oil Extract A of step (b) as a phytoestrogenic bioactive emulsifying agent for the composition comprising the Extract C and Extract D with therapeutically effective amount of vitamin E and a therapeutically effective amount of one bioavailable form of magnesium with the Extract B (soluble fiber) as binding agent to form a stable composition rich in phytoestrogens and phytochemicals of fenugreek in a stable compressible form for ameliorating, treating and/or preventing peri- and post-menopausal discomforts in a subject suffering from peri- or post-menopausal symptoms.

In another embodiment, the composition further comprises excipient material suitable for use in preparation of dosage forms for administration in the oral, parenteral, rectal or transdermal mode. Suitable excipients include without limitations fenugreek galactomannans, guar gum, gum Arabic, xanthan gum, tamarind gum, glucomannans, gum ghatti, tara gum psilium gum. Non-limiting examples include non-toxic compatible fillers, binders such as starch, polyvinyl pyrrolidone or cellulose ethers, disintegrants such as sodium starch glycolate, crosslinked polyvinyl pyrrolidone or croscarmellose sodium, buffers, preservatives, anti-oxidants, lubricants, flavorings, thickeners, coloring agents, wetting agents such as sodium lauryl sulfate, emulsifiers and the like. The amount of excipient or additive can range from about 0.1 to about 95 weight percent of the total weight of the treatment composition or therapeutic combination.

Disclosed herein is a method of ameliorating, treating and/or preventing peri- and post-menopausal symptoms in a subject suffering from peri- or post-menopausal discomforts comprising administering to the subject a therapeutically effective amount of the nutraceutical composition comprising extract of *Trigonella foenum-graecum*; at least one bioavailable form of magnesium and vitamin E.

Appropriate menopausal symptoms include without limitations acne, aches, hot flashes, rapid heartbeats, irritability, fatigue, insomnia, nervousness, high levels of stress, extreme sweating, headaches, frequent urination, early wakening, vaginal dryness, mood swings, depression, dizziness, cardiac symptoms, appetite changes, night sweats, cold flashes and osteopenia.

In an embodiment, a subject suffering from peri- or post-menopausal discomfort is administered a daily dose of the composition comprising a therapeutically effective amount of the nutraceutical composition comprising extract of *Trigonella foenum-graecum*; at least one bioavailable form of magnesium and vitamin E for a period of time from 10 to 100 days, wherein the daily dose comprises from about 0.25 to about 2.0 g of the composition/kg body weight.

An amount of an invention composition sufficient to treat a symptom of menopause is thus an amount of the sufficient to reduce the frequency of the menopausal symptom, ameliorate the severity of the symptom, or both. In general, the amount needed to treat a symptom will depend upon the subject's age, weight, general health, genetic makeup, emotional condition, and other factors. An amount of the nutraceutical composition suitable for a daily dose will be equivalent to about 0.004 to 0.035 grams of the composition of the invention per kilogram body weight of the subject, preferably about 0.008 to about 0.17 grams per kilogram body weight of the subject.

In an embodiment, the nutraceutical composition is provided in a daily dose in a range of about 200 to 1600 mg of dry extract per kg body weight, more preferably about 400 to about 800 mg of dry extract per kg body weight.

The person skilled in the art will recognize that the dose necessary to achieve the desired symptom-relieving effect within the stipulated ranges may be titrated and will likewise recognize that upward or downward deviations from those ranges may be tolerated within the scope of the present invention.

In view of the prominent property of promoting phytoestrogenic activity and general healthcare of the reproductive system by the extracts in a subject, further embodiment of the present invention includes a method comprising the step of administrating orally or topically to the subject an effective amount of an extract derived from fenugreek seeds.

In an embodiment, a method of ameliorating, treating and/or preventing peri- and post-menopausal symptoms in a subject in need of such a treatment is provided comprising administering to the subject a therapeutically effective amount of the composition comprising a therapeutically effective amount of the extract of *Trigonella foenum-graecum*; a therapeutically effective amount of at least one bioavailable form of magnesium and a therapeutically effective amount of vitamin E as a hormone replacement therapy.

In an embodiment, the composition of the present invention may be provided in combination with a therapeutic agent. Appropriate therapeutic agents include without limitations androgens, estrogens, progestins, their pharmaceutically acceptable salts and derivatives.

The daily dosage for the various compositions and therapeutic combinations described above can be administered to a patient in a single dose or in multiple sub-doses, as desired. Sub-doses can be administered 1 to 3 times per day. Sustained release dosages can be used.

Advantageously the composition of the present invention shows the beneficial effects of increase in serum estradiol levels and serum calcium levels, enhanced calcium absorption, energy levels, vitality, mood and libido and potentially reduces the menopause related adverse symptoms including but not limited to hot flashes, anxiety, depression, insomnia, night sweatiness and irritations in the post-menopausal subjects. Clinical and Nutrition intervention evaluation for assessment of dietary intake, anthropometric measurements, lifestyle pattern and its improvement, subjective evaluation of menopausal symptoms and frequency of occurrence of menopausal symptoms among women during menopause shows beneficial effects of the composition. The decrease in menopausal problems and improvement in the quality of life can be attributed mainly to the balancing effect of the present composition on estradiol hormone. In addition, the composition is safe with no adverse effects on the levels of cardiovascular factors, hematological or biochemical parameters as seen in the clinical studies.

Exemplary Embodiments

Embodiment A is a nutraceutical composition comprising extract of *Trigonella foenum-graecum*; at least one bioavailable form of magnesium and vitamin E, characterized in that the composition is stable, directly compressible, water soluble, free flowing form having particle size not more than 2.0 μm.

Embodiment B is the composition of Embodiment A, wherein the extract of *Trigonella foenum-graecum* comprises phytoestrogens comprising at least one of a steroidal saponin selected from the group comprising protodioscin, diosgenin and yamogenin; an alkaloid, trigonellin; and, a non-proteinogenic amino acid, 4-hydroxyisoleucine.

Embodiment C is the composition of Embodiment A, wherein the phytoestrogens present in 1 g of the composition is at an equivalent dose of 15 to 30 g of *Trigonella foenum-graecum* seeds in natural state.

Embodiment D is the composition of Embodiment A, wherein the vitamin E comprises alpha-, beta-, gamma-, or delta-tocopherol or tocotrienol, or a mixture thereof in free form or in the form of salts.

Embodiment E is the composition of Embodiment A, wherein the at least one bioavailable form of magnesium is selected from a group comprising, magnesium citrate, magnesium hydroxide and magnesium stearate.

Embodiment F is the composition of Embodiment A, further comprising at least one of a protein fraction, a carbohydrate fraction, a fat fraction, a fiber fraction, or a combination thereof, wherein the fractions are derived from fenugreek seeds.

Embodiment G is the composition of Embodiment A, wherein the composition comprises protodioscin in the range of about 5 to 20 g, trigonellin in the range of about 1 to 8 g, 4-hydroxyisoleucine in the range of about 1 to 10 g, proteins in the range of about 1 to 15 g, carbohydrates in the range of about 5 to 25 g, dietary fibers in the range of about 2 to 15 g, fat in the range of about 2-10 g, vitamin E in the range of about 5 to 20 g and magnesium citrate in the range of about 10 to 25 g in 100 g dry powder of the composition.

Embodiment H is the composition of Embodiment A in the form of a solid, semi-solid or liquid suitable for administration in the oral, parenteral, rectal or transdermal mode.

Embodiment I is the composition of Embodiment A is an orally administrable dietary supplement or a nutrient supplement.

Embodiment J is a process for producing a nutraceutical composition comprising: (a) mechanically reducing the seeds of *Trigonella foenum-graecum* to obtain size-reduced particles, (b) subjecting the particles of step (a) to solvent extraction to obtain an Extract A, (c) separating the particles of step (a) or the extracted particles of step (b) into lighter and heavier fractions based on density using a gravity separator, (d) subjecting the lighter fraction obtained from step (c) to solvent extraction and subsequent drying to obtain an Extract B, (e) subjecting the heavier fraction obtained from step (c) to solvent extraction to obtain a micelle, (f) separation of the micelle of step (e) into two portions whereby:

i. the first portion is concentrated under reduced pressure to obtain a liquid phytonutrient rich Extract C having phytoestrogen content in the range of 3 to 8% protodioscin, ii. the second portion is concentrated and purified to obtain a phytonutrient rich liquid Extract D having phytoestrogen content in the range of 10 to 40% protodioscin, (g) evaporation of the liquid extracts of step (f) such that the water content is 70 to 90% and ethanol content less than 0.5% and (h) blending vitamin E with the Extract A obtained from steps (b) and further mixing into a 1 to 3% water solution of Extract B obtained from step (d) followed by addition of the Extract C and Extract D of step (g) with at least one bioavailable form of magnesium to form a nutraceutical composition, wherein the ratio of Extract C to Extract D is in the range of about 4:1 to about 1:4 and the resulting blend is stable, water soluble having particle size preferably less than 2 μm, suitable for the conversion into free flowing powder or granular form.

Embodiment K is the process of Embodiment J, wherein the mechanical reduction is by cutting, flaking and/or powdering to a particle size of less than 5 mm, preferably to a particle size of 0.5 mm to about 1.5 mm.

Embodiment L is the process of Embodiment J, wherein the extraction of step (b) is solvent extraction with aliphatic alkanes or supercritical fluid extraction and phytochemicals other than oil are not extracted.

Embodiment M is the process of Embodiment J, wherein the solvent extraction of step (d) and (e) is carried out by organic solvents comprising lower aliphatic alcohols, lower aliphatic ketones and mixtures thereof either alone or in combination with water.

Embodiment N is the process of Embodiment J, wherein the concentration of step (f) and (g) is by evaporation at reduced pressure at 600 to 700 atmosphere and a temperature below 50° C.

Embodiment O is the process of Embodiment J, wherein the purification of step (f)(ii) is by chromatography, precipitation and liquid-liquid extraction, preferably by adsorption or ion-exchange chromatography.

Embodiment P is the process of Embodiment J, wherein optionally the blended composition comprises Extract A and Extract B with vitamin E and at least one bioavailable form of magnesium to form a nutraceutical composition having stable, readily compressible, water soluble, free flowing form.

Embodiment Q is a method of ameliorating, treating and/or preventing peri- and post-menopausal discomforts in a subject suffering from peri- or post-menopausal symptoms comprising administering to the subject a therapeutically effective amount of the nutraceutical composition of Embodiment A.

Embodiment R is a method of Embodiment Q, wherein the menopausal symptom is selected from a group comprising acne, aches, hot flashes, rapid heartbeats, irritability, fatigue, insomnia, nervousness, high levels of stress, extreme sweating, headaches, frequent urination, early wakening, vaginal dryness, mood swings, depression, dizziness, cardiac symptoms, appetite changes, night sweats, cold flashes and osteopenia.

Embodiment S is a method of Embodiment Q, wherein the subject is administered a daily dose of the nutraceutical composition for a period of time from 10 to 100 days, wherein the daily dose comprises from about 0.25 to about 2.0 g of the composition.

Embodiment T is a method of Embodiment Q, wherein an effective amount of the nutraceutical composition is administered as a hormone replacement therapy.

EXAMPLES

The following examples are set forth to further exemplify the invention and are not intended to be limiting thereof. There are a variety of alternative techniques and procedures available to those of skill in the art that would similarly permit one to successfully practice the intended invention. All specific materials and methods described below, in whole or in part, fall within the scope of the invention. These specific compositions, materials, and methods are not intended to limit the invention, but merely to illustrate specific embodiments falling within the scope of the invention. It will be understood that many variations can be made in the procedures herein described while still remaining within the bounds of the invention. It is the intention of the inventors that such variations are included within the scope of the invention.

Example 1

Preparation of Nutraceutical Composition (FHE-3010)

Diagrammatic representation of the preparation is provided in FIG. 1.

Step 1. Preparation of Fenugreek Oil (Extract A)

Supercritical carbon dioxide (SCFE-CO2) extraction was carried out using supercritical fluid extractor with CO2 cycle system. The extractor vessel with 3×24 Litre capacities was loaded with 10 kg of powdered fenugreek seeds with a particle size of 0.5 to 5 mm mesh. Food grade liquid CO2 was delivered to extraction vessel using high pressure pump. Extraction pressure was at 15 to 20 mPa and 40° C., most preferably at 18 mPa. The pressure in the extraction vessel was controlled by back pressure regulator. Heat exchangers were provided in system to maintain temperature in the extractor and separator vessel. Extract A was collected every 20 min and 60 min taken for complete extraction to get golden yellow oil of fenugreek without extracting the phytochemicals. The extracted oil was filtered through 125 micron cloth. The residue or the defatted powder comprises the phytochemicals such as saponins, amino acids, and alkaloids.

Step 2. Preparation of Fenugreek Soluble Fiber (FSF) Fraction (Extract B)

100 kg of dried fenugreek seeds or defatted powder of Step 1 were coarse ground in a hammer mill or cut into 0.5 to 3 mm pieces and subjected to separation into lighter (30 Kg) and heavier fraction (70 Kg) based on the density, using a gravity separator. Heavier fractions were of 0.72±0.2 g/mL and lighter fractions were of 0.45±0.2 g/mL density.

30 kg of the lighter fraction was further ground in a hammer mill with a 3 to 5 mm sieve. The ground fraction was sieved with a 20 mesh into bigger particles comprising primarily the endosperm of fenugreek seeds rich in soluble dietary fiber like galactomannans and proteins and 20 mesh passing smaller particles.

20 mesh retained bigger particles was further extracted with 90 to 99% ethyl alcohol purity at 60 to 70° C. temperature. Extraction was repeated 3 to 7 times and the residue was dried under vacuum, most preferably in a rotary vacuum paddle drier. The dried residue was further ground in a micro-pulverizer for 3 to 10 min, most preferably 5 min. The powder was again sieved through 20 mesh and the retained fraction was collected. The retained fraction was further ground such that the powder was able to pass through a size 80 mesh.

The resulting powder Extract B was found to have a unique composition of 70 to 80% soluble dietary fiber, 10 to 16% proteins, 3 to 5% of insoluble fiber and less than 5% moisture as white powder with 15 to 30 g/mL water holding or swelling capacity.

Step 3. Preparation of Fenugreek Husk Extract (FHE-1) (Extract C)

Around 70 Kg of the heavier fraction rich in fenugreek husk obtained from step 2 was flaked on a roller flaker to obtain particle size of 0.2 to 1 mm thickness.

The reduced particles were subjected to extraction with ethyl alcohol/water mixture in a stainless steel vessel fitted with an agitator, steam jacket, solvent inlet pipes and chilled water condenser. A mixture of ethanol/water, most preferably containing 70% v/v of ethanol, was used in a ratio of 1:3 w/v and circulated for 2 h at 20° C. to 50° C. The filtrate was stored in a separate tank. The extraction, as described above, was repeated two more times.

The combined filtrate, called micelle, was then evaporated under reduced pressure to contain less than 1000 ppm ethanol level to obtain a free flowing dark brown liquid. This fluid contains the phytochemicals, namely, saponins, trigonellin, 4-hydroxyiosleucine, proteins and carbohydrates. The water solution thus obtained was spray dried or freeze dried to obtain a free flowing powder Extract C. The Gravimetric analysis of the Extract C was found to contain a total of 42% saponin content. The average composition of phytochemicals in Extract C is as provided in Table 1 below:

TABLE 1

| Phytochemical make-up in Extract C | |
|---|---|
| Components | Average wt content |
| Protodioscin | 60 mg/g |
| Trigonellin | 76 mg/g |
| 4-Hydroxyisoleucine | 69 mg/g |
| Soluble fiber | 50 mg/g |
| Protein | 43 mg/g |
| Fat | 25 mg/g |
| Carbohydrates | 412 mg/g |

Step 4. Preparation of Fenugreek Husk Extract (FHE-2) (Extract D)

Concentrated ethanol extract obtained in Step 3 was dissolved in water to a brix level of 10 to 20%, most preferably 10 to 14%. The solution was then passed through an adsorbent column filled with divinylbenzene—cross-linked polystyrene macro-porous resin at 0.75 to 1.2 column volume/hour. The eluent was collected separately and again passed through the column in a similar way and repeated 3 to 4 times. The column was then washed with water at a flow rate of 1 to 2 column volume/hour Finally the column was eluted with 70 to 95% ethanol at a flow rate of 0.75 to 1.2 column volume/hour.

The eluent was evaporated to a pasty mass at 45° C. to 55° C. under vacuum. The residue mass was further dissolved in water at 20 to 25% brix and subjected to spray drying or freeze drying conditions, to obtain a free flowing powder Extract D (FHE-2 of FIG. 1).

Gravimetric analysis of the Extract D reveals a total of 53% saponin content present in the extract. The average composition of phytochemicals in Extract D is as follows:

TABLE 2

Phytochemical make-up in Extract D

| Components | Average wt content |
|---|---|
| Protodioscin | 290 mg/g |
| Trigonellin | 6 mg/g |
| 4-Hydroxyisoleucine | NIL |
| Soluble fiber | 50 mg/g |
| Protein | 70 mg/g |
| Carbohydrates | 295 mg/g |

Step 5. Formulation of Composition FHE-3010

3 g of Extract B prepared as 80 mesh size powder was dissolved in 300 mL of water and homogenized under 250 bar pressure at 35 to 40° C. employing a double stage pressure homogenizer.

5 mL of Extract A (fenugreek oil) was further mixed with 13 g of natural Vitamin E (Tocopherol E). Vitamin E sourced naturally comprises mixed tocopherols of $\alpha$-(86 mg/g), ($\beta$-(12.1 mg/g), $\gamma$-(448 mg/g) and $\delta$-tocopherol (173 mg/g).

The Extract A-vitamin E mixture was slowly added to the homogenized Extract B at 20000 to 25000 rpm using a rotor-stator homogenizer to obtain a microemulsion of 1 to 2 μm particle size resulting in an emulsion of fenugreek oil-vitamin E and Extract B (FSF).

Extract C (FHE-1) and Extract D (FHE-2) each 32.5 g were mixed together and dissolved in 650 mL of water. 20 g of magnesium citrate was then dissolved in this Extract solution. This solution was further slowly added to the emulsion of fenugreek oil-vitamin E and Extract B (FSF) under constant stirring at 2000 to 4000 rpm.

The mixture was then homogenized in a double stage high pressure homogenizer at 200-250 bar first cycle followed by 450 to 600 bar second cycle at below 45° C. to get micelles of 1±0.5 μm particle size. The homogenate composition obtained is spray dried at inlet temperature 130-160° C. and outlet temperature 90° C. to 100° C. to produce free flowing powder with ethanol solvent concentration less than 100 ppm and moisture less than 5%.

The resultant free flowing powder composition comprises bioactive components like phytoestrogens and phytochemicals in a highly concentrated form such that 1 g of the composition in powder form corresponds to bioactive components obtained from 15 to 25 g of fenugreek seeds.

A schematic representation of the preparation of the composition FHE-3010 is provided in FIG. 1. The phytoestrogen rich composition FHE 3010 is found to have a general nutrient make-up as provided below in Table 3. The FSF fraction (Extract B) containing soluble fiber galactomannans provides sufficient gum-like character for its mechanical strength. Therefore, the current formulation of FHE 3010 is in a powder form suitable for the formulation of tablets upon direct compression in a tableting machine.

TABLE 3

Nutrient make-up of the composition (FHE 3010)

| Content | Amount (g/100 g) |
|---|---|
| Protodioscin | 10-18 |
| Trigonellin | 3-4 |
| 4-Hydroxyisoleucine | 3-5 |
| Proteins | 5-10 |
| Carbohydrates | 10-20 |
| Fat | 4-5 |
| Dietary fiber | 5-10 |
| Tocopherol (Vitamin E) | 10-15 |
| Magnesium citrate | 10-15 |

Example 2

Stability of the Nutraceutical Composition (FHE 3010)

Stability studies of the nutraceutical composition of Example 1 (FHE 3010) were carried out using a protocol prepared by following the International Conference on Harmonization (ICH) guidelines.

The sample packets of 10 g of the composition were incubated at 40° C.±2° C. and 75±5% relative humidity for a period of 6 months in a stability chamber (Remi, Mumbai, India). The samples were withdrawn at 0, 1, 2, 3, and 6 months and analyzed for various physicochemical parameters such as saponins, protodioscin, trigonellin, 4-hydroxyisoleucine, total carbohydrate, proteins, fat, moisture content etc. The pH stability of the aqueous solution was checked by preparing 5% (w/w) solutions at pH 2.0, 5.0, and 6.8 using hydrochloric acid and phosphate buffers. Magnesium levels were determined by direct aspiration into the flame atomic absorption spectrophotometer. Temperature stability was verified by maintaining a 5% aqueous solution of FHE3010 at 90±2° C. for 30 min. The results are provided in the Table 4 below.

TABLE 4

Storage stability of composition (FHE 3010).

| Parameter | 0 month | 1 month | 2 months | 3 months | 6 months |
|---|---|---|---|---|---|
| Appearance | Pale Brown | Pale Brown | Pale Brown | Pale Brown | Pale Brown |
| Odour | Characteristic-Fenugreek | Characteristic-Fenugreek | Characteristic-Fenugreek | Characteristic-Fenugreek | Characteristic-Fenugreek |
| Moisture (%) | 2 | 2 | 2.05 | 2.1 | 2.1 |
| Fat | 4.7 | 4.7 | 4.6 | 4.7 | 4.7 |
| Bulk density (g mL$^{-1}$) | 0.41 | 0.41 | 0.41 | 0.41 | 0.41 |
| Carbohydrates (g per 100 g) | 19.5 | 19.6 | 19.5 | 19.4 | 19.5 |
| Dietary Fiber | 8.91 | 8.9 | 8.9 | 8.9 | 8.89 |
| Protein (g per 100 g) | 7.6 | 7.6 | 7.55 | 7.5 | 7.5 |
| Saponin | 41.5 | 41.0 | 42.4 | 41.3 | 40.4 |

TABLE 4-continued

Storage stability of composition (FHE 3010).

| Parameter | 0 month | 1 month | 2 months | 3 months | 6 months |
|---|---|---|---|---|---|
| Protodioscin | 15.2 | 14.9 | 15.1 | 15.2 | 15.0 |
| Trigonellin | 3.6 | 3.5 | 3.3 | 3.4 | 3.5 |
| 4-hydroxyisoleucine | 4.1 | 4.0 | 3.85 | 3.8 | 3.79 |
| Microbiology | | | | | |
| Total plate count | 400 cfu g$^{-1}$ | 390 cfu g$^{-1}$ | 410 cfu g$^{-1}$ | 390 cfu g$^{-1}$ | 400 cfu g$^{-1}$ |
| Yeast & Mould | 30 cfu g$^{-1}$ | 25 cfu g$^{-1}$ | 30 cfu g$^{-1}$ | 35 cfu g$^{-1}$ | 30 cfu g$^{-1}$ |
| Coliforms | <3 MPN g$^{-1}$ | <3 MPN g$^{-1}$ | <3 MPN g$^{-1}$ | <3 MPN g$^{-1}$ | <3 MPN g$^{-1}$ |
| E. coli | Absent/g | Absent/g | Absent/g | Absent/g | Absent/g |
| Salmonella Others | Absent/g | Absent/g | Absent/g | Absent/g | Absent/g |
| Vitamin E (g per 100 g) | 13.8 | 13.7 | 13.2 | 13.1 | 13.2 |
| Magnesium (g per 100 g) | 12.6 | 12.6 | 12.5 | 12.5 | 12.3 |

Example 3

Preparation of Nutraceutical Composition Into Solid Dose Form (FHE-3010) For Oral Administration The FHE 3010 powder is formulated as granules of 20 to 80 mesh suitable for filling into hard-shell two-piece capsules. Granulation is done with or without additional excipients by both dry and wet granulation methods.

Dry granulation is done with compact granulator where the powder containing 5 to 10% moisture is compacted in a roller compactor to form hard flakes which are dried and subjected to granules by using an oscillating granulator and sieving.

Wet granulation is performed on powder with 10 to 20% moisture content using a high shear rapid mixture granulator followed by drying and sieving. Excipients like gum acacia, cellulose, PVP and the like is added to increase the mechanical strength.

Example 4

Safety Evaluation of Composition (FHE-3010) in Pre-Clinical Studies

All animal experiments were carried out in strict accordance with the ethical norms approved by the Institutional Animal Ethics Committee (IAEC) recognized by the Committee for the Purpose of Control and Supervision of Experiments on Animals (CPCSEA), Government of India (Registration No: 1620/pO/RcBi/S/12/CPCSEA).

Acute Toxicity Studies

Twenty four Wistar rats having 180 to 200 g body weight were divided into four groups, each consisting of three male and three female rats as follows.

Group I (Normal) was administered with the vehicle (1 mL water) and Groups II, III and IV were orally administered with FHE 3010 at doses of 0.5, 1.5 and 3 g per kg body weight respectively. The animals were observed for 24 h for any signs of toxicity, mortality, and adverse reactions.

FHE-3010 was further administered at a maximum practical dosage of 3000 mg/kg body weight to Wistar rats of both sexes for 14 days by oral gavage and the animals were observed for 24 h for any signs of toxicity, mortality, and adverse reactions.

Sub-Chronic Toxicity Studies

Forty Wistar rats (20 males and 20 females) of average body weight between 180 to 200 g were selected by stratified randomization and then divided into four groups, each consisting of five males and five females of approximately the same body weight treated as follows.

Group I was the normal control administered with 1 mL of water containing 5% Tween 80; Group II, III and IV were administered with FHE-3010 at doses of 0.25, 0.5 and 1.0 g per kg body weight respectively. FHE-3010 was suspended in distilled water containing 5% Tween 80 and orally administered to the animals using an oral needle in such a way that all the animals received same volume of vehicle. The animals were monitored during the study period of 90 days for any type of clinical symptoms, mortality, and adverse reactions of the administered extract. Body weight and food consumption were determined every week up to 90 days.

TABLE 5

Effect of 90 days administration of FHE-3010 on the weight of various organs in male and female Wistar rats

| Treatments | Liver (g) | Kidney (g) | Heart (g) | Spleen (g) |
|---|---|---|---|---|
| MALE | | | | |
| Control (No treatments) | 9.42 ± 0.49 | 2.05 ± 0.17 | 1.06 ± 0.09 | 0.80 ± 0.09 |
| FHE-3010 250 mg/Kg | 7.65 ± 0.91 | 1.62 ± 0.36 | 0.86 ± 0.16 | 0.90 ± 0.09 |
| FHE-3010 500 mg/Kg | 8.46 ± 1.03 | 1.89 ± 0.25 | 0.93 ± 0.09 | 0.82 ± 0.05 |
| FHE-3010 1000 mg/Kg | 8.81 ± 0.42 | 1.71 ± 0.05 | 0.97 ± 0.13 | 0.81 ± 0.11 |
| FEMALE | | | | |
| Control (No treatments) | 9.46 ± 2.21 | 2.12 ± 0.57 | 1.02 ± 0.23 | 0.79 ± 0.09 |
| FHE-3010 250 mg/Kg | 9.36 ± 0.62 | 2.01 ± 0.17 | 1.02 ± 0.09 | 0.85 ± 0.08 |

TABLE 5-continued

Effect of 90 days administration of FHE-3010 on the weight
of various organs in male and female Wistar rats

| Treatments | Liver (g) | Kidney (g) | Heart (g) | Spleen (g) |
|---|---|---|---|---|
| FHE-3010 500 mg/Kg | 9.67 ± 0.94 | 1.93 ± 0.09 | 1.02 ± 0.10 | 0.77 ± 0.08 |
| FHE-3010 1000 mg/Kg | 7.59 ± 1.04 | 1.58 ± 0.19 | 0.85 ± 0.10 | 0.92 ± 0.15 |

Data expressed as mean ± SD of animals in a group (n = 5)

TABLE 6

Effect of 90 days administration of FHE-3010 on various biochemical
parameters in male and female Wistar rats

MALE

| | | FHE-3010 | | |
|---|---|---|---|---|
| Parameters | Control | 250 mg/Kg | 500 mg/Kg | 1000 mg/Kg |
| Total Cholesterol (mg/dl) | 46.3 ± 9.3 | 50 ± 24.7 | 51.7 ± 7.5 | 51.8 ± 10.9 |
| Triglycerides (mg/dl) | 61.6 ± 38.3 | 55.3 ± 14.7 | 52.1 ± 23.2 | 49.6 ± 8.2 |
| HDL (mg/dl) | 22.8 ± 4.2 | 27.4 ± 7.9 | 26.7 ± 4.6 | 26.3 ± 3.8 |
| LDL (mg/dl) | 10.9 ± 2.7 | 16.9 ± 16.9 | 9.8 ± 2.9 | 14.4 ± 8.8 |
| ALT (U/L) | 63.5 ± 26.9 | 72 ± 14.8 | 64.1 ± 24 | 66.9 ± 16.6 |
| AST (U/L) | 142 ± 25.2 | 147.6 ± 16.1 | 138.4 ± 19.4 | 135.8 ± 24.6 |
| ALP (U/L) | 117.9 ± 34.9 | 104.9 ± 25.5 | 111.5 ± 39.8 | 144 ± 55.6 |
| Total Protein (mg/dl) | 7.6 ± 0.4 | 7.9 ± 0.6 | 8.1 ± 0.5 | 8 ± 0.6 |
| Creatinine (mg/dl) | 0.9 ± 0.1 | 0.9 ± 0.1 | 0.9 ± 0.1 | 0.8 ± 0.1 |
| Sodium (mmol/L) | 134.6 ± 4.9 | 135.8 ± 5.9 | 135.8 ± 3.2 | 133.6 ± 4 |
| Potassium (mmol/L) | 3.5 ± 0.6 | 3.7 ± 0.6 | 4.1 ± 0.6 | 4.3 ± 0.3 |

FEMALE

| | | FHE-3010 | | |
|---|---|---|---|---|
| Parameters | Control | 250 mg/Kg | 500 mg/Kg | 1000 mg/Kg |
| Total Cholesterol (mg/dl) | 52.3 ± 6.8 | 52.3 ± 16.1 | 64.9 ± 17.2 | 65.9 ± 4.6 |
| Triglycerides (mg/dl) | 60.7 ± 21.8 | 40.4 ± 12.7 | 51.9 ± 13.1 | 67.2 ± 24 |
| HDL (mg/dl) | 27.7 ± 4.9 | 29.1 ± 4.6 | 30.8 ± 4.6 | 28.6 ± 1.3 |
| LDL (mg/dl) | 17.1 ± 5.4 | 16.5 ± 9.1 | 25.8 ± 9.4 | 23.3 ± 11.3 |
| ALT (U/L) | 55.3 ± 7.3 | 59.7 ± 12 | 66.4 ± 17.3 | 50.7 ± 12.8 |
| AST (U/L) | 155.4 ± 20.1 | 150.6 ± 15 | 147.2 ± 37.1 | 155.2 ± 25.8 |
| ALP (U/L) | 104.6 ± 60.3 | 93.5 ± 33.3 | 98.4 ± 49.8 | 127.7 ± 42.2 |
| Total Protein (mg/dl) | 7.9 ± 0.4 | 8.2 ± 0.2 | 8.2 ± 0.7 | 7.8 ± 0.4 |
| Creatinine (mg/dl) | 0.8 ± 0.1 | 0.9 ± 0.1 | 0.9 ± 0 | 0.9 ± 0 |
| Sodium (mmol/L) | 133.4 ± 3.1 | 137.4 ± 3.3 | 137.4 ± 2.8 | 132 ± 5.2 |
| Potassium (mmol/L) | 3.9 ± 0.2 | 3.9 ± 0.3 | 3.7 ± 0.8 | 3.4 ± 0.7 |

TABLE 7

Effect of chronic administration of FHE-3010 on hematological
parameters in male and female Wistar rats

MALE

| | FHE-3010 | | |
|---|---|---|---|
| Control | 250 mg/Kg | 500 mg/Kg | 1000 mg/Kg |
| 8.6 ± 4.5 | 11 ± 5.1 | 10.3 ± 4.7 | 12.1 ± 4.2 |
| 14.3 ± 2.6 | 11.8 ± 3.8 | 13.5 ± 3.8 | 12.5 ± 3.4 |
| 12.2 ± 0.8 | 12.8 ± 0.8 | 12.3 ± 0.5 | 12.4 ± 0.8 |
| 674 ± 132.7 | 690.6 ± 114.4 | 639.6 ± 118 | 668.2 ± 193.4 |

FEMALE

| | FHE-3010 | | |
|---|---|---|---|
| Control | 250 mg/Kg | 500 mg/Kg | 1000 mg/Kg |
| 9.8 ± 3.4 | 10.8 ± 4.4 | 8.1 ± 1.2 | 9.6 ± 3.9 |
| 12.6 ± 2.9 | 14.8 ± 1.2 | 11.9 ± 2.8 | 12.9 ± 2.5 |
| 12.5 ± 1 | 13.5 ± 1.1 | 12.7 ± 1.1 | 13.1 ± 0.5 |
| 586.6 ± 148.4 | 595 ± 127.2 | 496.8 ± 154.3 | 642.6 ± 146.9 |

Figure 2:
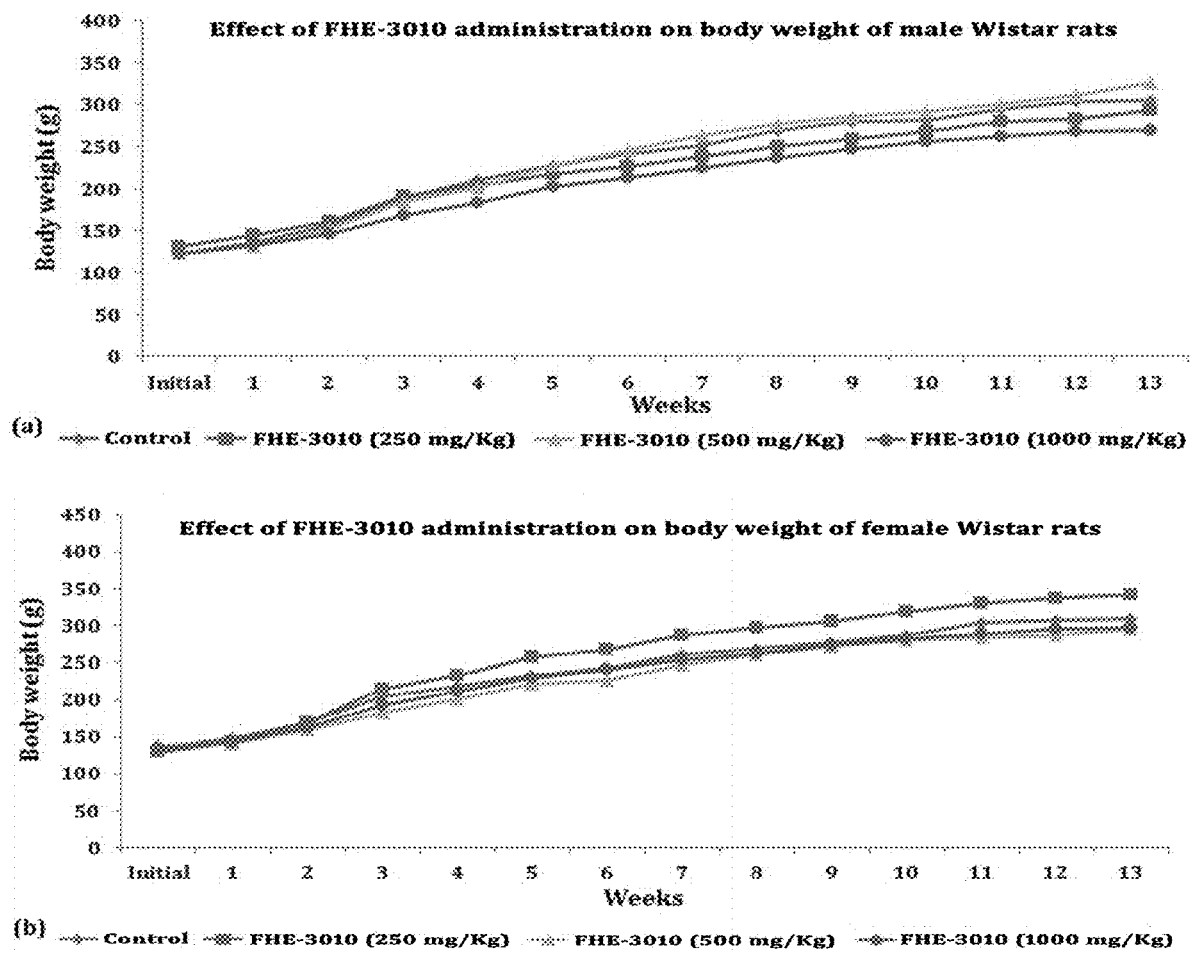
FIG. 2 shows the effect of a nutraceutical composition (FHE-3010) administration on the body weight increase in male (a) and female (b) Wistar rats.
Figure 3:
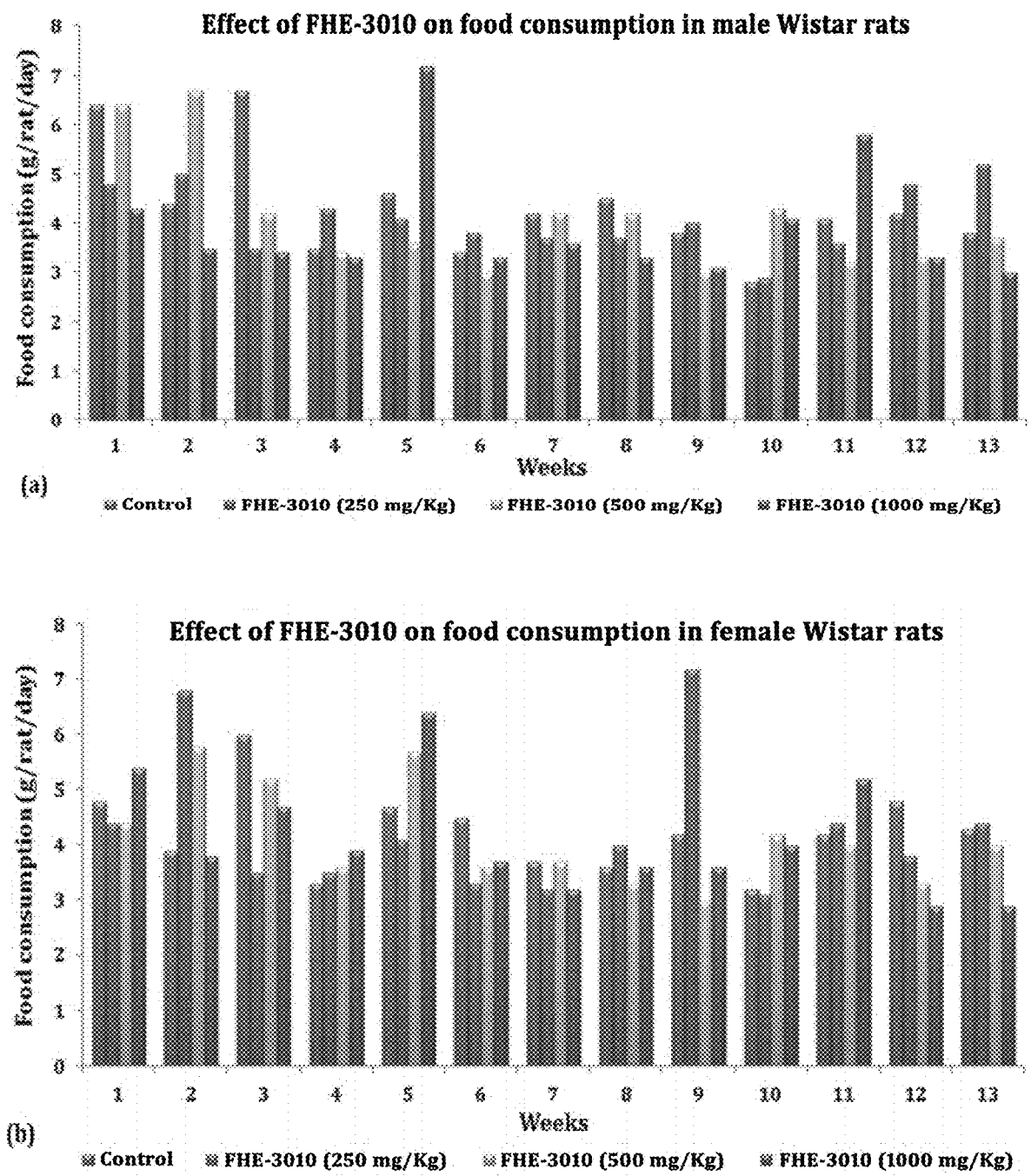
FIG. 3 shows the effect of a nutraceutical composition (FHE-3010) administration on the food consumption in male (a) and female (b) Wistar rats.

FIGS. 2 and 3 show the effect of the composition on body weight and food consumption. Food and water intake and body weight changes were similar to those of the normal control group of animals, indicating that FHE3010 has no detrimental effect upon growth patterns, since these indicators can show the adverse effects of drugs and chemicals.

In the chronic study, no mortality or adverse effects was observed either on the daily food intake or growth. The composition did not induce any signs of toxicity, or behavioural changes during the acute study period. Hematological constants were on par with control. Biochemical measurements in serum and liver of the FHE administered rats revealed no appreciable changes in any of the parameters such as enzyme levels of ALT (alanine aminotransferase), AST (aspartate aminotransferase) and ALP (alkaline phosphatase), as well as various serum constituents such as total protein, cholesterol, creatinine and electrolytes at any of the dietary levels.

Histological Studies

For histological studies, animals were sacrificed by cervical dislocation under ether anesthesia. All the organs were examined visibly for any type of abnormalities in the structure. The blood was collected by direct heart puncture method into EDTA coated and non-EDTA vials for analyzing hematological parameters and serum biochemistry.

Figure 4:
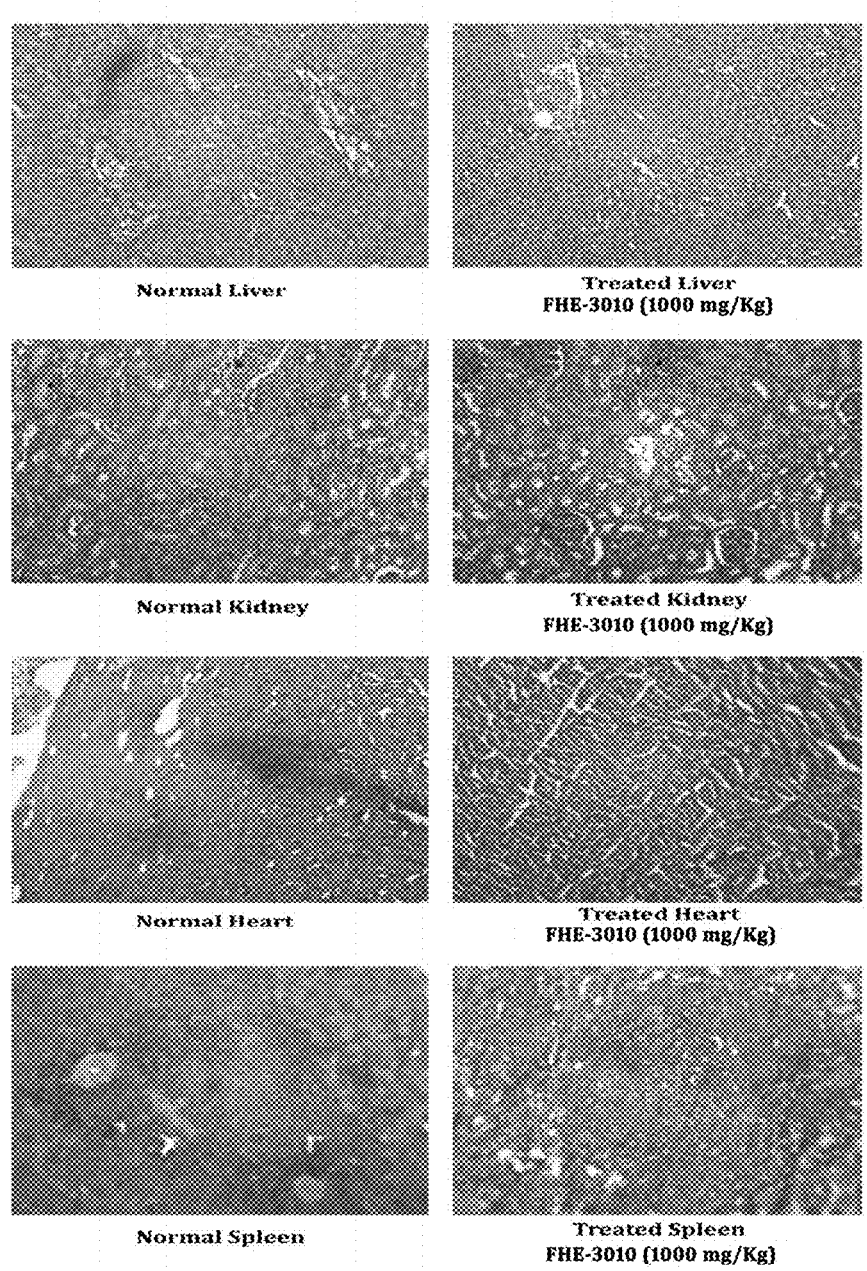
FIG. 4 shows the histology of various internal organs of Wistar rats administered a nutraceutical composition (FHE-3010).

Terminal autopsy revealed no alterations in relative organ weights of various vital organs, or their histo-architecture (Table 5). Histopathology of the liver, kidney, heart and spleen did not show any abnormalities among FHE 3010 treated animals, indicating the absence of any adverse toxicological effects from FHE-3010 administration at a dose of 1 g/Kg body weight for 13 weeks as shown in FIG. 4. The histology of liver from normal rat showed portal triads, bile ducts, central venous system and hepatocytes morphology arranged in trabecular pattern. Sinusoidal space and Kupffer cells were normal. The liver of treated animals also showed portal area with normal vasculature and normal biliary ducts. Normal lymphocytic collections, hepatocytes found to be arranged in cords. Kupffer cells and sinusoidal spaces were normal.

The histology of kidney from normal rat showed glomeruli with normal Bowman's capsule and renal tubules. The interstitial tissues showed normal appearance, except for a few dilated blood vessels.

The kidney of treated animals also showed normal architecture. Glomeruli appeared normal with normal Bowman's capsule, and renal tubes were normal. Interstitial tissues show normal appearance except for a few hemorrhagic areas.

The sections from the heart tissue of normal rats showed cardiac muscle with branching of the muscle fibers, centrally placed nuclei and intercalated discs with normal architecture. The results were similar in the case of treated animals also. There was no inflammation or damages detected.

The spleen tissues from normal animals were with normal lymphoid follicles showing germinal centres. The sinusoidal spaces were congested and contained degenerating RBCs. Many siderophages were also present along with histiocytes. There was no abnormality detected in the tissues sections from the treated animals also.

Example 5

Clinical Studies to Evaluate the Effect of FHE-3010 on Peri- and Post-Menopausal Discomforts Study Design and Setting 90 days randomized, double-blind, placebo-controlled study on healthy peri- and post-menopausal women was conducted at Sri Jayadeva Institute of Cardiovascular Sciences & Research, Bangalore, Karnataka, India. The protocol was evaluated and approved by the Institutional ethical committee clearance (IEC) and written consent from all individuals was obtained before the study, as per the protocol suggested by the Government of India.

FHE-3010 used in the present investigation was found to have a 41.3% total saponin content (gravimetric analysis) with an average composition of phytochemicals comprising protodioscin (136 mg/g), trigonellin (31 mg/g), 4-Hydroxyisoleucine (33 mg/g), dietary fiber (78 mg/g), protein (62 mg/g) and carbohydrates (155 mg/g) along with 125 mg/g vitamin E and 180 mg/g magnesium citrate.

Subject Selection

A total of 50 women subjects between 45 to 60 years age, who are in peri- or post-menopausal stage and experiencing various menopausal discomforts with minimum 3 hot flashes per day were selected by purposive sampling, and 12 of these women refused to participate, leaving 38 women and were randomly assigned to receive FHE-3010 (n=20) or placebo (n=18).

Out of 20 subjects, 16 subjects completed FHE-3010 treatment (n=16) and placebo (n=15). Sequentially numbered and sealed plastic airtight containers of the same shape and size containing FHE-3010 (250 mg) or placebo capsules were used to conceal the allocation and to maintain the blinding Every container contained 60 capsules of FHE-3010 or placebo. The participants were instructed to take two capsules per day (1 after breakfast and 1 after dinner) for 1 week so as to adjust with the intake of FHE-3010 physiologically and later on advised to take 4 capsules per day (2 after breakfast and 2 after dinner) for another 12 weeks. The subjects were monitored telephonically on a weekly basis and direct consultation after 90 days of supplementation.

The primary evaluation of the efficacy data were measured at baseline and after 90 days of treatment and values are expressed as mean ±SD. The statistical significance was compared between untreated and treated groups by one way analysis of variance (ANOVA) followed by an appropriate post hoc test (Tukey's multiple comparison test) using Graphpad InStat software (version 3.05). A p value<0.05 was considered statistically significant.

Effect of FHE-3010 on Quality of Life (QoL) of Postmenopausal Subjects

SF-36® (The Health Institute, Boston, Mass., USA) Health Survey questionnaire composed of 36 questions was scored to measure eight aspects of the quality of life: general physical and mental health state, physical and social functioning, physical and emotional health, pain, and vitality (Ware & Sherbourne, 1992. Data were collected at baseline prior to the treatment, and also after the intervention.

The results from the assessment of quality of life with SF-36 questionnaire showed improvement in mental and physical health of all participating subjects following Fenugreek extract treatment. The subjects clearly reported a significant increase in their overall health functioning, in particular, general well-being (27.93% increase, p<0.05) and mental health (18.97% increase, p<0.05) when compared to baseline; however, similar increases were not found in placebo group. Likewise the mental and physical component scores were significantly improved with FHE-3010 supplementation as shown in Table 7 below.

TABLE 8

Scores on the SF-36 scale following FHE-3010 treatment and placebo. Data are given as the mean ± standard deviation (n = 15).

| Measures | Placebo | | FHE-3010 | |
|---|---|---|---|---|
| | Before | After | Before | After |
| Physical functioning | 41.8 ± 8.6 | 40.6 ± 11.8$^d$ | 43.4 ± 7.4$^d$ | 49.5 ± 6.8$^{a,a}$ |
| Role physical | 42.4 ± 7.4 | 41.8 ± 9.6$^d$ | 41.2 ± 9.2$^d$ | 51.3 ± 11.6$^{a,a}$ |
| Bodily pain | 44.8 ± 10.2 | 42.7 ± 12.8$^d$ | 43.8 ± 8.7$^d$ | 48.6 ± 6.9$^{a,a}$ |
| General health | 43.7 ± 11.4 | 43.4 ± 9.8$^d$ | 38.6 ± 8.2$^d$ | 47.2 ± 10.8$^{a,a}$ |

TABLE 8-continued

Scores on the SF-36 scale following FHE-3010 treatment and placebo.
Data are given as the mean ± standard deviation (n = 15).

| Measures | Placebo Before | Placebo After | FHE-3010 Before | FHE-3010 After |
|---|---|---|---|---|
| Vitality | 40.9 ± 14.8 | 40.2 ± 13.4$^d$ | 42.3 ± 11.9$^d$ | 53.8 ± 8.2$^{a,a}$ |
| Social functioning | 43.5 ± 8.2 | 43.1 ± 9.4$^d$ | 39.8 ± 8.6$^d$ | 48.2 ± 7.9$^{a,a}$ |
| Role emotional | 46.5 ± 12.5 | 45.2 ± 9.9$^d$ | 46.8 ± 13.2$^d$ | 49.2 ± 12.8$^{a,a}$ |
| Mental health | 44.4 ± 14.4 | 44.2 ± 12.6$^d$ | 41.2 ± 8.6$^d$ | 47.9 ± 7.3$^{a,a}$ |
| Physical component score | 41.9 ± 12.2 | 41.2 ± 14.6$^d$ | 39.6 ± 9.7$^d$ | 50.6 ± 11.2$^{a,a}$ |
| Mental component score | 42.6 ± 14.3 | 40.3 ± 11.8d | 42.6 ± 12.5$^d$ | 50.5 ± 10.6$^{a,a}$ |

Data are given as mean ± SD.
Comparison between groups before and after placebo treatment found non-significant (d = p > 0.05), while FHE-3010 treatment compared to placebo (final) and FHE-3010 (initial) showed statistical significance (a = p < 0.05)

Menopause Symptom Assessment

Greene climacteric scale (GCS) was used to assess the symptoms of menopause. GCS is a comprehensive validated tool consisting of 21 questions that women use to rate how much they are bothered by the symptoms. It consisted of eleven statements pertained to psychiatric symptoms, and included two parts, anxiety and depression. Seven statements assessed physical aspects and two assessed vasomotor symptoms. The final statement considered sexual desire disorder. The severity of the symptoms was scored as zero (no symptoms), one (mild), two (moderate), and three (severe) based on self-reporting. Data were collected at baseline prior to the treatment, and also after the intervention.

Figure 5:
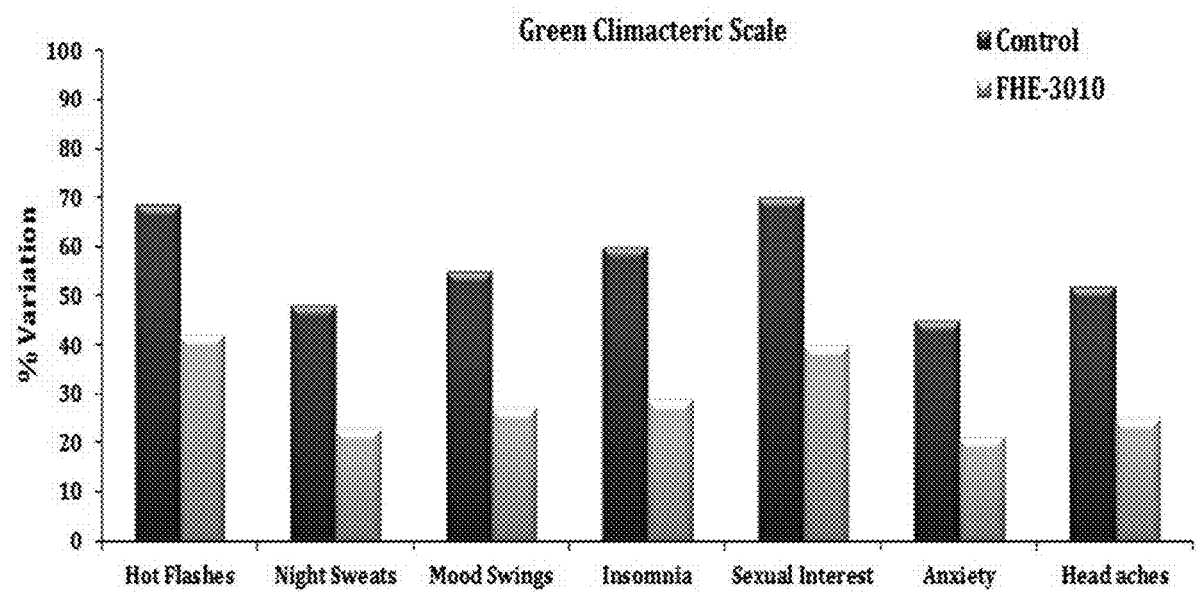
FIG. 5 shows the influence of 3 months supplementation of a nutraceutical composition (FHE-3010) on GCS in menopausal women (n=5).

At baseline, the mean ±SD of the GCS total score was 34.83±6.87 in the FHE-3010 group and 37.25±7.45 in the placebo group, with no significant difference. In addition, the groups had approximately near scores for all GCS subscales. The GCS total score in the FHE-3010 treated group was significantly lower than that in the placebo supplemented group at the end of the study [95% confidence interval: −14.15 (−16.43 to −11.87), p<0.001]—FIG. 5. The treatment group also showed significantly more improvement than the control group in all GCS subscale scores (psychological, vasomotor, physical, and sexual symptoms). The anxiety scale showed a significant improvement following FHE-3010 treatment, when compared to both the baseline and placebo with a reduction of 58.92% (with respect to the baseline) and 53.94% (with respect to the placebo) respectively (p<0.001). The measured subscale depression also showed a significant reduction in scores on treatment with FHE-3010 in comparison to either baseline (47.7%) or after placebo (50%) respectively, p<0.001). In addition, physical and vasomotor symptoms were significantly decreased by 63.72% (baseline) and 54.20% (Placebo) respectively (p<0.001) when compared to baseline (FIG. 5).

Safety of FHE-3010 as Revealed by the Biochemical/Hematological Analysis

Blood was collected from each patient by vein puncture and taken into EDTA/non EDTA vials for assaying hematological parameters such as hemoglobin, random blood sugar, lipid profile, estradiol, and serum calcium levels. The hematological analysis of postmenopausal women was done at baseline and after 3 months of supplementation at 1g/day level.

Haemoglobin (Hb) content was determined using a hematology analyzer (Model-Diatron, Wein, Austria) and random blood sugar levels were checked using enzymatic UV test (hexokinase method) (Neeley, 1972). Serum calcium levels were estimated by O-cresolphthalein method (Stern & Lewis, 1957) and the serum estradiol levels were measured using automated electro- chemiluminescence immunoassay (ECLIA) (Lee et al., 2006). Total cholesterol levels were estimated by the CHOD-PAP (cholesterol oxidase–phenol+aminophenazone) enzymatic method (Deeg & Ziegenhorn, 1983), triglycerides by the GPO-PAP (glycerol-3-phosphate oxidase–phenol+aminophenazone) method and HDL cholesterol by precipitation with phosphotungistic acid (Assmann et al., 1983). VLDL cholesterol was estimated by the Friedewald equation (VLDL=triglyceride/5) and LDL cholesterol by the equation LDL=total cholesterol−(HDL+VLDL) (DeLong et al., 1986).

Figure 6:
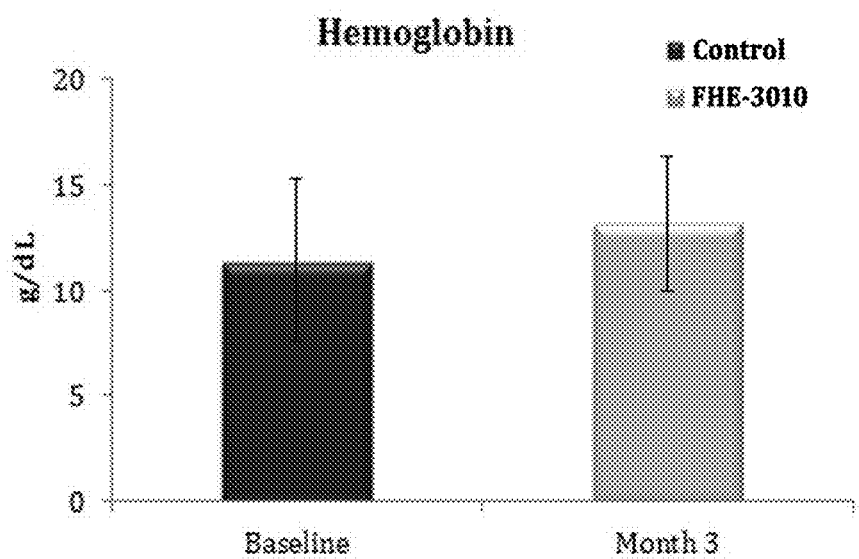
FIG. 6 shows the influence of 3 months supplementation of a nutraceutical composition (FHE-3010) on hemoglobin levels in menopausal women (n=5). Data expressed as mean±SD.
Figure 7:
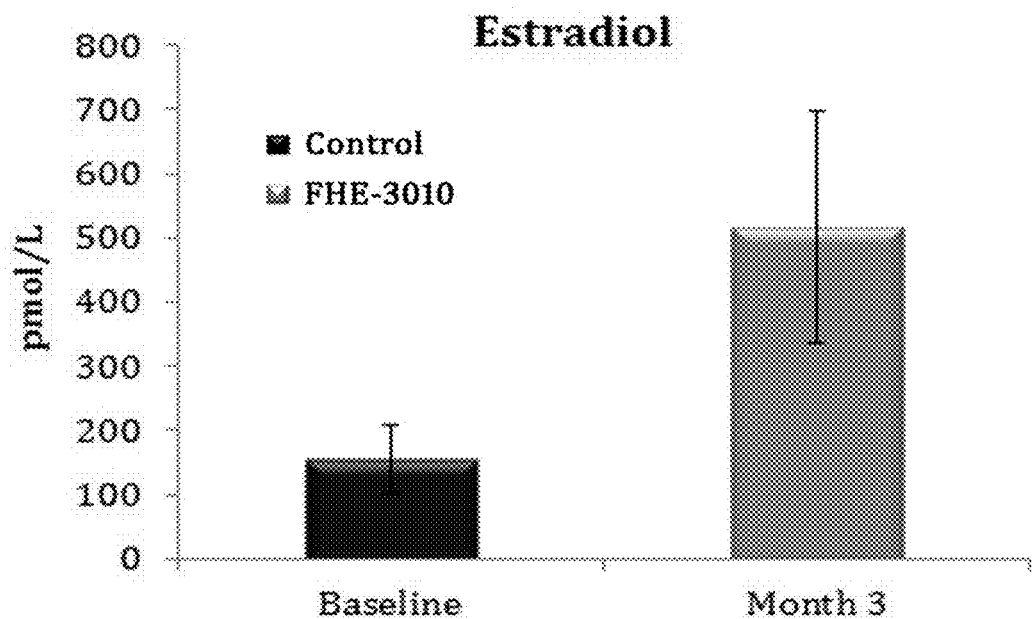
FIG. 7 shows the influence of 3 months supplementation of a nutraceutical composition (FHE-3010) on estradiol levels in menopausal women (n=5). Data expressed as mean±SD.
Figure 8:
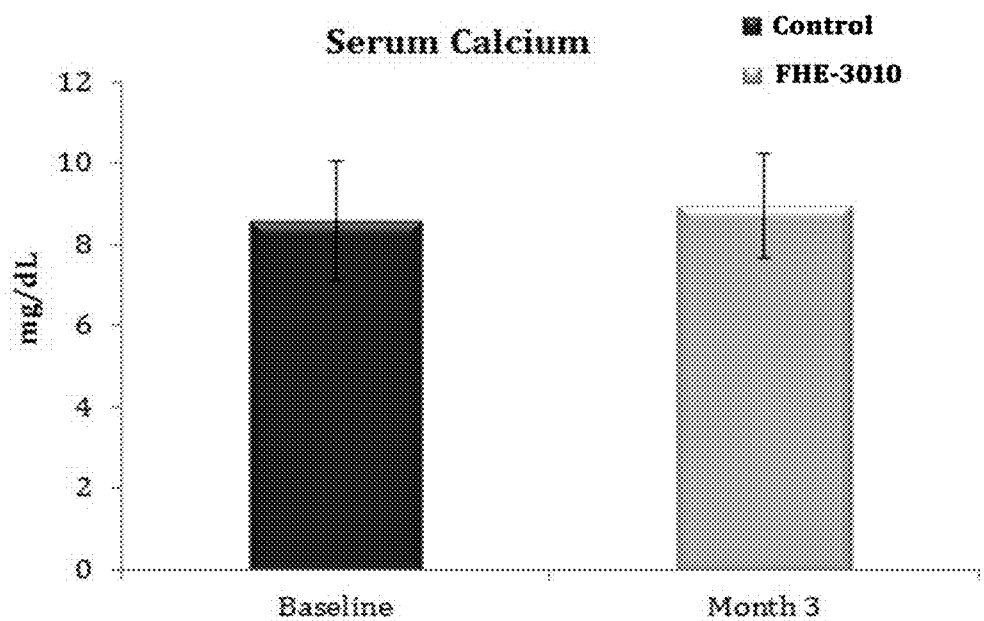
FIG. 8 shows the influence of 3 months supplementation of a nutraceutical composition (FHE-3010) on serum calcium levels in menopausal women (n=5). Data expressed as mean±SD.

The hematological and biochemical evaluation showed that there were no adverse variations in the parameters like hemoglobin or random blood sugar levels and the cardiovascular risk factors such as total cholesterol, triglycerides, LDL, HDL, VLDL levels, even after supplementing FHE-3010 for 13 weeks and which shows the safety of the formulation, while the formulation resulted in reducing various risk factors associated with cardiac health Table 9 below. However the results also showed significant enhancement in the serum calcium levels in the FHE-3010 supplemented group, while no beneficial effects were seen in placebo supplemented group (FIGS. 6 to 8).

TABLE 9

Safety of FHE-3010 and hematology/lipid profile of FHE-3010 supplemented postmenopausal women

| Parameters | Placebo Before | Placebo After | FHE-3010 Before | FHE-3010 After |
|---|---|---|---|---|
| Systolic BP (mmHg) | 128.4 ± 12.5 | 127.6 ± 14.2 | 124.7 ± 18.4 | 123.3 ± 21.2 |
| Diastolic BP (mmHg) | 85.2 ± 16.4 | 88.2 ± 14.7 | 82.8 ± 12.6 | 84.2 ± 14.6 |
| Hb (g dL$^{-1}$) | 11.8 ± 4.22 | 11.6 ± 3.40 | 11.2 ± 4.20 | 13.6 ± 2.80 |
| RBS (mg dL$^{-1}$) | 119.7 ± 24.50 | 124.6 ± 21.24 | 121.5 ± 26.40 | 112.6 ± 18.70 |
| Estradiol (pmol L$^{-1}$) | 143.6 ± 62.36 | 124.30 ± 57.28 | 146.5 ± 53.80 | 562.8 ± 139.7 |
| Serum Calcium (mg dL$^{-1}$) | 8.72 ± 1.4 | 8.24 ± 1.56 | 8.78 ± 1.49 | 9.28 ± 1.21 |
| Lipid Profile | | | | |
| Cholesterol (mg dL$^{-1}$) | 218.8 ± 21.4 | 220.4 ± 31.2 | 221.6 ± 34.6 | 192.6 ± 46.8 |
| Triglycerides (mg dL$^{-1}$) | 204.2 ± 32.3 | 216.5 ± 42.4 | 210.8 ± 41.7 | 171.2 ± 54.2 |
| HDL (mg dL$^{-1}$) | 44.1 ± 11.2 | 42.8 ± 13.7 | 48.8 ± 9.6 | 54.5 ± 11.4 |

TABLE 9-continued

Safety of FHE-3010 and hematology/lipid profile of FHE-3010 supplemented postmenopausal women

| Parameters | Placebo | | FHE-3010 | |
|---|---|---|---|---|
| | Before | After | Before | After |
| LDL (mg dL$^{-1}$) | 116.2 ± 14.8 | 120.8 ± 18.2 | 112.7 ± 12.6 | 96.8 ± 8.2 |
| VLDL (mg dL$^{-1}$) | 40.2 ± 11.4 | 38.6 ± 14.8 | 36.8 ± 14.5 | 32.8 ± 12.6 |

Effect of FHE-3010 on the Anthropometric Measurements

Anthropometric data of postmenopausal women at the baseline and after 3 months of supplementation at 1g/day level were undertaken. The measurements included body mass index (BMI=weight/height$^2$), mid-arm circumference, waist circumference, hip circumference and waist/hip ratio were measured as per the guidelines specified by Jelliffe (1966). All anthropometric measures were taken under fasting conditions, and participants were wearing light-weight clothing and no shoes. The body mass index (BMI=weight/height$^2$) was used to assess weight variation. Weight was evaluated using a digital scale. Height was measured in standing position using a tape meter to the nearest 0.5 cm. Waist circumference was measured to the nearest 0.5 cm midway between the lowest rib margin and the top of iliac crest, and hip circumference at the largest posterior extension of the buttocks. Both were measured to the nearest 1 cm with an inelastic tape. Measurements were taken at the end of a normal respiration while subjects stood erect with arms hanging loosely at sides and feet were together. The waist/hip ratio was used to assess body fat distribution considering<0.8 as a gynecoid pattern and≥0.8 as an android pattern.

The postmenopausal participants were overweight with increased body fat percentage and waist circumference. Overweight and obesity were present in 27% and 49%, of the participants, respectively. The anthropometric measurements are presented in Table 10. It was observed that there was slight beneficial variation in the anthropometric measurements. The total weight, BMI and mid-arm, hip and waist circumferences were found to be decreased after 13 weeks in those women who have completed the FHE-3010 intervention, while in the placebo group no beneficial effects were seen. Even though the anthropometric measurements were found to be decreased, the results were not statistically significant (p>0.05) as seen in the table below.

Effect of FHE-3010 on the Hemoglobin (Hb) and Random Blood Sugar (RBS) Levels

Blood was collected from each patient by vein puncture and taken into EDTA vials for assaying hematological parameters such as hemoglobin and random blood sugar. The hematological analysis was done at baseline prior to the treatment, and also after the intervention. Haemoglobin (Hb) content was determined using a hematology analyzer (Model-Diatron, Wein, Austria) and random blood sugar levels were checked using enzymatic UV test (hexokinase method) (Neeley, 1972).

The hematological and biochemical evaluation showed that there were no adverse variations in the parameters like hemoglobin or random blood sugar levels. The hemoglobin levels were found to be improved in the FHE-3010 supplemented group (FIG. 6).

Effect of FHE-3010 on the Serum Estrogen and Calcium Levels

Ten post-menopausal women having their mean blood estradiol level in the lower range (150 pmol/L) were supplemented with FHE-3010 for 90 days at 1 g/day level and blood estradiol and calcium level was again measured on 91$^{st}$ day. Serum calcium levels were estimated by O-Cresolphthalein method (Stern & Lewis, 1957) and estradiol levels were measured using automated electro-chemiluminescence immunoassay (ECLIA) (Lee et al., 2006).

It was found that mean level of estradiol showed a significant enhancement to 550 pmol/L (FIG. 7). Serum calcium level showed an enhancement from 8.58 to 8.94 mg/dL (FIG. 8), and haemoglobin levels showed significant enhancement indicating the therapeutic efficacy of FHE 3010 supplemented group. The estradiol levels were found to show 2× (120%) increase up on FHE 3010 supplementation, while in the case of placebo group there was a reduction of 2% in estradiol levels (FIG. 6). Serum calcium levels showed an improvement of 2% in FHE 3010 treated

TABLE 10

Individual and Anthropometric characteristics of postmenopausal subjects supplemented with FHE-3010

| Parameters | Placebo (n = 15) | | FHE-3010 (n = 16) | |
|---|---|---|---|---|
| | Before | After | Before | After |
| Age (years) | 51.57 ± 9.62 | 51.57 ± 9.62 | 55.2 ± 9.88 | 55.2 ± 9.88 |
| Height (cm) | 151.92 ± 8.25 | 151.92 ± 8.25 | 152.54 ± 7.62 | 152.54 ± 7.62 |
| Weight (Kg) | 62.74 ± 12.63 | 64.65 ± 14.36 | 65.28 ± 13.41 | 62.51 ± 15.11 |
| Body Mass Index (Kg/m$^2$) | 27.18 ± 5.69 | 28.01 ± 6.73 | 28.05 ± 4.85 | 26.86 ± 5.21 |
| Mid Arm Circumference (cm) | 32.41 ± 3.26 | 32.84 ± 4.16 | 30.27 ± 3.63 | 28.25 ± 3.44 |
| Waist Circumference (cm) | 101.16 ± 14.21 | 101.59 ± 12.65 | 98.93 ± 11.29 | 96.17 ± 12.83 |
| Hip Circumference (cm) | 112.36 ± 10.95 | 113.10 ± 12.42 | 110.74 ± 12.60 | 108.52 ± 11.33 |
| Waist:Hip ratio | 0.90 | 0.90 | 0.90 | 0.89 | group and a 0.75% reduction exhibited by placebo group (FIG. 8). The enhancement of the hormone levels were also supported by the reduction of overall percentage in various symptoms associated with menopause in these individuals. The symptoms such as hot flushes, night sweats, mood swings, irritability, headache, insomnia etc. were found to be reduced to a greater extent in women supplemented with FHE 3010, when compared to the placebo group.

However, the above-mentioned changes in estradiol, hemoglobin, serum calcium and the effect on quality of life were significantly high as compared to the group of subjects treated with FHE1 (Extract C) and FHE2 (Extract D) separately, indicating the significance of the formulation of FHE3010 and the synergistic effect of magnesium and vitamin E in the formulation of fenugreek extract. While FHE1 and FHE2 produced an elevation of 134 and 252 pmol/L of elevation in estradiol, FHE 3010 produced 400 units of enhancement. Though the observed enhancement in serum calcium level with FHE3010 was from 8.58 to 8.94 mg/dL, FHE 1 and FHE2 does not provide a significant enhancement. When the Quality of Life (QoL) was compared by SF-36 questionnaire, the enhancement in the overall QoL index was 42% with FHE3010, as compared to FHE1 and FHE2 which produced only 14 and 26% improvements indicating the synergetic effect of the micronutrients with phyto-estrogenic extracts.

The use of examples anywhere in this specification including examples of any terms discussed herein is illustrative only, and in no way limits the scope and meaning of the invention or of any exemplified term. Likewise, the invention is not limited to various embodiments given in this specification. It is to be understood that both the foregoing general description and the following detailed description are exemplary and explanatory only and are not restrictive of the invention, as claimed.

The invention claimed is:

1. A nutraceutical composition comprising extract of *Trigonella foenum-graecum*; at least one bioavailable form of magnesium and vitamin E, characterized in that the composition is stable, directly compressible, water soluble, free flowing form having particle size not more than 2.0 µm.

2. The composition of claim 1, wherein the extract of *Trigonella foenum-graecum* comprises at least one of a steroidal saponins selected from the group consisting of protodioscin, diosgenin and yamogenin; an alkaloid, and, a non-proteinogenic amino acid.

3. The composition of claim 1, wherein the vitamin E comprises any form of biologically active tocopherol, or a mixture of tocopherols and tocotrienols from any natural source comprising alpha, beta-, gamma-, or delta-tocopherols or tocotrienols, or a mixture thereof in free form or in the form of salts.

4. The composition of claim 1, wherein the at least one bioavailable form of magnesium is selected from a group consisting of, magnesium citrate, magnesium hydroxide and magnesium stearate.

5. The composition of claim 1, further comprising at least one of a protein fraction, a carbohydrate fraction, a fat fraction, a fiber fraction, or a combination thereof, wherein the fractions are derived from fenugreek seeds.

6. The composition of claim 1, wherein the composition comprises protodioscin in the range of about 5 to 20 g, trigonellin in the range of about 1 to 8 g, 4-hydroxyisoleucine in the range of about 1 to 10 g, proteins in the range of about 1 to 15 g, carbohydrates in the range of about 5 to 25 g, dietary fibers in the range of about 2 to 15 g, fat in the range of about 2-10 g, vitamin E in the range of about 5 to 20 g and magnesium citrate in the range of about 10 to 25 g in 100 g dry powder of the composition.

7. The composition of claim 1 in the form of a solid, semi-solid or liquid suitable for administration in the oral, parenteral, rectal or transdermal mode.

8. The composition of claim 1 as an orally administrable dietary supplement or a nutrient supplement.

9. The composition of claim 2, wherein the alkaloid includes trigonellin, and the non-proteingenic amino acid includes 4-hydroxyisoleucine.

10. The composition of claim 3, wherein the biologically active tocopherol includes alpha D tocopherol.

* * * * *